(12) United States Patent
Bender et al.

(10) Patent No.: US 10,398,565 B2
(45) Date of Patent: Sep. 3, 2019

(54) LIMITED PROFILE INTERVERTEBRAL IMPLANT WITH INCORPORATED FASTENING AND LOCKING MECHANISM

(71) Applicant: Choice Spine, LLC, Knoxville, TN (US)

(72) Inventors: Mark W Bender, Gainesville, FL (US); Steven J Norton, Gainesville, FL (US); Jason A. McAtamney, Austin, TX (US); Larry G. Hickey, Alachua, FL (US)

(73) Assignee: CHOICE SPINE, LLC, Knoxville, TN (US)

( * ) Notice: Subject to any disclaimer, the term of this patent is extended or adjusted under 35 U.S.C. 154(b) by 0 days.

(21) Appl. No.: 15/360,399

(22) Filed: Nov. 23, 2016

(65) Prior Publication Data

US 2017/0135822 A1     May 18, 2017

Related U.S. Application Data

(63) Continuation-in-part of application No. 14/260,869, filed on Apr. 24, 2014, now Pat. No. 9,517,144.

(51) Int. Cl.
*A61F 2/44*      (2006.01)
*A61F 2/30*      (2006.01)
(Continued)

(52) U.S. Cl.
CPC .......... *A61F 2/447* (2013.01); *A61F 2/30749* (2013.01); *A61F 2/30771* (2013.01); *A61F 2/4455* (2013.01); *A61F 2/4611* (2013.01); *A61F 2/4637* (2013.01); *A61B 17/0642* (2013.01); *A61F 2002/3093* (2013.01); *A61F 2002/30476* (2013.01); *A61F 2002/30528* (2013.01); *A61F 2002/30565* (2013.01);
(Continued)

(58) Field of Classification Search
CPC ...... A61F 2/4455; A61F 2/446; A61F 2/4465; A61F 2/447; A61F 2002/30579
See application file for complete search history.

(56) References Cited

U.S. PATENT DOCUMENTS 3,848,601 A     11/1974    Ma et al.
3,867,728 A     2/1975     Substad et al.
(Continued)

FOREIGN PATENT DOCUMENTS

WO     2007035892     3/2007

*Primary Examiner* — Ellen C Hammond
(74) *Attorney, Agent, or Firm* — Luedeka Neely Group, PC

(57) ABSTRACT

In some embodiments, an intervertebral implant may include a body including a superior and an inferior surface. The implant may include a first channel extending from an anterior end towards the posterior end of the body. The implant may include a first anchor channel. The implant may include a first guide member positionable in the first channel. The implant may include a first anchor. When the first guide member moves from a first position to a second position the first anchor may be conveyed through the first anchor channel and couple the body to an adjacent vertebra. In some embodiments, the implant may include a first locking mechanism which inhibits, during use, the first guide member from moving from the second position to the first position upon activation of the first locking mechanism.

20 Claims, 14 Drawing Sheets

(51) Int. Cl.
  *A61B 17/064* (2006.01)
  *A61F 2/46* (2006.01)
(52) U.S. Cl.
  CPC .............. *A61F 2002/30579* (2013.01); *A61F 2002/30904* (2013.01); *A61F 2002/4642* (2013.01)

(56) References Cited

U.S. PATENT DOCUMENTS

| | | |
|---|---|---|
| 4,309,777 A | 1/1982 | Patil |
| 4,349,921 A | 9/1982 | Kuntz |
| 4,611,581 A | 9/1986 | Steffee |
| 4,657,550 A | 4/1987 | Daher |
| 4,696,290 A | 9/1987 | Steffee |
| 4,743,260 A | 5/1988 | Burton |
| 4,759,766 A | 7/1988 | Buettner-Janz et al. |
| 4,759,769 A | 7/1988 | Hedman et al. |
| 4,763,644 A | 8/1988 | Webb |
| 4,772,287 A | 9/1988 | Ray et al. |
| 4,790,303 A | 12/1988 | Steffee |
| 4,854,311 A | 8/1989 | Steffee |
| 4,863,476 A | 9/1989 | Shepperd |
| 4,863,477 A | 9/1989 | Monson |
| 4,907,577 A | 3/1990 | Wu |
| 4,911,718 A | 3/1990 | Lee et al. |
| 4,932,975 A | 6/1990 | Main et al. |
| 4,946,378 A | 8/1990 | Hirayama et al. |
| 4,946,458 A | 8/1990 | Harms et al. |
| 5,042,982 A | 8/1991 | Harms et al. |
| 5,047,055 A | 9/1991 | Bao et al. |
| 5,059,194 A | 10/1991 | Michelson |
| 5,071,437 A | 12/1991 | Steffee |
| 5,092,867 A | 3/1992 | Harms et al. |
| 5,108,438 A | 4/1992 | Stone |
| 5,123,926 A | 6/1992 | Pisharodi |
| 5,171,278 A | 12/1992 | Pisharodi |
| 5,171,281 A | 12/1992 | Parsons et al. |
| 5,180,393 A | 1/1993 | Commarmond |
| 5,192,326 A | 3/1993 | Bao et al. |
| 5,196,013 A | 3/1993 | Harms et al. |
| 5,207,678 A | 5/1993 | Harms et al. |
| 5,217,497 A | 6/1993 | Mehdian |
| 5,246,458 A | 9/1993 | Graham |
| 5,258,031 A | 11/1993 | Salib et al. |
| 5,261,909 A | 11/1993 | Sutterlin et al. |
| 5,306,307 A | 4/1994 | Senter et al. |
| 5,306,309 A | 4/1994 | Wagner et al. |
| 5,314,477 A | 5/1994 | Marnay |
| 5,320,644 A | 6/1994 | Baumgartner |
| 5,336,223 A | 8/1994 | Rogers |
| 5,370,697 A | 12/1994 | Baumgartner |
| 5,375,823 A | 12/1994 | Navas |
| 5,397,364 A | 3/1995 | Kozak et al. |
| 5,401,269 A | 3/1995 | Buettner-Janz et al. |
| 5,403,315 A | 4/1995 | Ashman |
| 5,415,661 A | 5/1995 | Holmes |
| 5,458,643 A | 5/1995 | Heggeness et al. |
| 5,423,816 A | 6/1995 | Lin |
| 5,425,773 A | 6/1995 | Boyd et al. |
| 5,443,467 A | 8/1995 | Biedermann et al. |
| 5,458,642 A | 10/1995 | Beer et al. |
| 5,480,401 A | 1/1996 | Navas |
| 5,496,321 A | 3/1996 | Puno et al. |
| 5,498,263 A | 3/1996 | DiNello et al. |
| 5,507,816 A | 4/1996 | Bullivant |
| 5,514,132 A | 5/1996 | Csernatony et al. |
| 5,514,180 A | 5/1996 | Heggeness et al. |
| 5,522,899 A | 6/1996 | Michelson |
| 5,527,314 A | 6/1996 | Brumfield et al. |
| 5,534,028 A | 7/1996 | Bao et al. |
| 5,534,029 A | 7/1996 | Shima |
| 5,534,030 A | 7/1996 | Navarro et al. |
| 5,540,688 A | 7/1996 | Navas |
| 5,545,165 A | 8/1996 | Biedermann et al. |
| 5,554,191 A | 9/1996 | Lahille et al. |
| 5,556,431 A | 9/1996 | Buettner-Janz |
| 5,562,663 A | 10/1996 | Wisnewski et al. |
| 5,562,737 A | 10/1996 | Graf |
| 5,562,738 A | 10/1996 | Boyd et al. |
| 5,571,109 A | 11/1996 | Bertagnoli |
| 5,609,635 A | 3/1997 | Michelson |
| 5,624,442 A | 4/1997 | Mellinger et al. |
| 5,645,599 A | 7/1997 | Samani |
| 5,653,763 A | 8/1997 | Errico et al. |
| 5,658,335 A | 8/1997 | Allen |
| 5,665,122 A | 9/1997 | Kambin |
| 5,672,175 A | 9/1997 | Martin |
| 5,672,176 A | 9/1997 | Biedermann et al. |
| 5,674,294 A | 10/1997 | Bainville et al. |
| 5,674,296 A | 10/1997 | Bryan et al. |
| 5,676,701 A | 10/1997 | Yuan et al. |
| 5,676,702 A | 10/1997 | Ratron |
| 5,683,391 A | 11/1997 | Boyd |
| 5,683,394 A | 11/1997 | Rinner |
| 5,683,464 A | 11/1997 | Wagner et al. |
| 5,702,450 A | 12/1997 | Bisserie |
| 5,725,527 A | 3/1998 | Biedermann et al. |
| 5,733,284 A | 3/1998 | Martin |
| 5,741,253 A | 4/1998 | Michelson |
| 5,755,797 A | 5/1998 | Baumgartner |
| 5,772,661 A | 6/1998 | Michelson |
| 5,776,199 A | 7/1998 | Michelson |
| 5,782,832 A | 7/1998 | Larsen et al. |
| 5,785,647 A | 7/1998 | Tompkins et al. |
| 5,797,909 A | 8/1998 | Michelson |
| 5,800,547 A | 9/1998 | Schafer et al. |
| 5,800,549 A | 9/1998 | Bao et al. |
| 5,800,550 A | 9/1998 | Sertich |
| 5,810,819 A | 9/1998 | Errico et al. |
| 5,810,820 A | 9/1998 | Santori et al. |
| 5,824,093 A | 10/1998 | Ray et al. |
| 5,824,094 A | 10/1998 | Serhan et al. |
| 5,827,328 A | 10/1998 | Buttermann |
| 5,836,960 A | 11/1998 | Kolesa et al. |
| 5,849,004 A | 12/1998 | Bramlet |
| 5,860,973 A | 1/1999 | Michelson |
| 5,861,041 A | 1/1999 | Tienboon |
| 5,863,293 A | 1/1999 | Richelsoph |
| 5,863,465 A | 1/1999 | Kinlen |
| 5,865,846 A | 2/1999 | Bryan et al. |
| 5,865,848 A | 2/1999 | Baker |
| 5,888,220 A | 3/1999 | Felt et al. |
| 5,888,226 A | 3/1999 | Rogozinski |
| 5,893,889 A | 4/1999 | Harrington |
| 5,895,427 A | 4/1999 | Kuslich et al. |
| 5,895,428 A | 4/1999 | Berry |
| 5,899,941 A | 5/1999 | Nishijima et al. |
| 5,928,243 A | 7/1999 | Guyer |
| 5,935,133 A | 8/1999 | Wagner et al. |
| 5,938,663 A | 8/1999 | Petreto |
| 5,951,555 A | 9/1999 | Rehak et al. |
| 5,961,518 A | 10/1999 | Errico et al. |
| 5,961,554 A | 10/1999 | Janson et al. |
| 5,964,769 A | 10/1999 | Wagner et al. |
| 5,976,186 A | 11/1999 | Bao et al. |
| 5,980,522 A | 11/1999 | Koros et al. |
| 5,984,967 A | 11/1999 | Zdeblick et al. |
| 5,989,250 A | 11/1999 | Wagner et al. |
| 5,989,290 A | 11/1999 | Biedermann et al. |
| 5,997,539 A | 12/1999 | Errico et al. |
| 6,001,130 A | 12/1999 | Bryan et al. |
| 6,017,344 A | 1/2000 | Errico et al. |
| 6,019,792 A | 2/2000 | Cauthen |
| 6,022,376 A | 2/2000 | Assell et al. |
| 6,030,389 A | 2/2000 | Wagner et al. |
| 6,039,763 A | 3/2000 | Shelokov |
| 6,045,552 A | 4/2000 | Zucherman et al. |
| 6,045,579 A | 4/2000 | Hochschuler et al. |
| 6,053,921 A | 4/2000 | Wagner et al. |
| 6,063,089 A | 5/2000 | Errico et al. |
| RE36,758 E | 6/2000 | Fitz |
| 6,080,193 A | 6/2000 | Hochschuler et al. |
| 6,093,205 A | 7/2000 | McLeod et al. |
| 6,096,038 A | 8/2000 | Michelson |

(56) References Cited

U.S. PATENT DOCUMENTS

| | | |
|---|---|---|
| 6,099,531 A | 8/2000 | Bonutti |
| 6,102,950 A | 8/2000 | Vaccaro |
| 6,106,526 A | 8/2000 | Harms et al. |
| 6,110,210 A | 8/2000 | Norton et al. |
| 6,113,637 A | 9/2000 | Gill et al. |
| 6,113,638 A | 9/2000 | Williams et al. |
| 6,123,707 A | 9/2000 | Wagner et al. |
| 6,126,689 A | 10/2000 | Brett |
| 6,132,430 A | 10/2000 | Wagner et al. |
| 6,132,464 A | 10/2000 | Martin |
| 6,132,465 A | 10/2000 | Ray et al. |
| 6,136,001 A | 10/2000 | Michelson |
| 6,136,031 A | 10/2000 | Middleton |
| 6,139,579 A | 10/2000 | Steffee et al. |
| 6,146,421 A | 11/2000 | Gordon et al. |
| 6,146,422 A | 11/2000 | Lawson |
| 6,156,067 A | 12/2000 | Bryan et al. |
| 6,159,244 A | 12/2000 | Suddaby |
| 6,162,252 A | 12/2000 | Kuras et al. |
| 6,165,218 A | 12/2000 | Husson et al. |
| 6,179,873 B1 | 1/2001 | Zientek |
| 6,179,874 B1 | 1/2001 | Cauthen |
| 6,186,034 B1 | 2/2001 | Lamons |
| 6,187,048 B1 | 2/2001 | Milner et al. |
| 6,200,348 B1 | 3/2001 | Biedermann et al. |
| 6,206,924 B1 | 3/2001 | Timm |
| 6,214,049 B1 | 4/2001 | Gayer et al. |
| 6,214,050 B1 | 4/2001 | Huene |
| 6,217,579 B1 | 4/2001 | Koros |
| 6,228,118 B1 | 5/2001 | Gordon |
| 6,231,609 B1 | 5/2001 | Mehdizadeh |
| 6,176,882 B1 | 6/2001 | Biedermann et al. |
| 6,241,730 B1 | 6/2001 | Alby |
| 6,264,656 B1 | 7/2001 | Michelson |
| 6,290,724 B1 | 9/2001 | Marino |
| 6,296,664 B1 | 10/2001 | Middleton |
| 6,315,797 B1 | 11/2001 | Middleton |
| 6,331,179 B1 | 12/2001 | Freid et al. |
| 6,348,071 B1 | 2/2002 | Steffee et al. |
| RE37,665 E | 4/2002 | Ralph et al. |
| 6,368,350 B1 | 4/2002 | Erickson |
| 6,368,351 B1 | 4/2002 | Glenn et al. |
| 6,371,990 B1 | 4/2002 | Ferree |
| 6,375,682 B1 | 4/2002 | Fleischmann et al. |
| 6,375,683 B1 | 4/2002 | Crozet et al. |
| 6,391,090 B1 | 5/2002 | Wagner et al. |
| 6,395,032 B1 | 5/2002 | Gauchet |
| 6,395,034 B1 | 5/2002 | Suddaby |
| 6,402,784 B1 | 6/2002 | Wardlaw |
| 6,402,785 B1 | 6/2002 | Zdeblick et al. |
| 6,409,766 B1 | 6/2002 | Brett |
| 6,413,259 B1 | 7/2002 | Lyons et al. |
| 6,416,515 B1 | 7/2002 | Wagner et al. |
| 6,419,703 B1 | 7/2002 | Fallin et al. |
| 6,419,704 B1 | 7/2002 | Ferree |
| 6,436,140 B1 | 8/2002 | Liu et al. |
| 6,440,168 B1 | 8/2002 | Cauthen |
| 6,442,814 B1 | 9/2002 | Landry et al. |
| 6,443,990 B1 | 9/2002 | Aebi et al. |
| 6,447,512 B1 | 9/2002 | Landry et al. |
| 6,447,544 B1 | 9/2002 | Michelson |
| 6,447,545 B1 | 9/2002 | Bagby |
| 6,447,546 B1 | 9/2002 | Bramlet et al. |
| 6,451,021 B1 | 9/2002 | Ralph et al. |
| 6,454,769 B2 | 9/2002 | Wagner et al. |
| 6,454,806 B1 | 9/2002 | Cohen et al. |
| 6,454,807 B1 | 9/2002 | Jackson |
| 6,475,218 B2 | 11/2002 | Gournay et al. |
| 6,478,822 B1 | 11/2002 | Leroux et al. |
| 6,478,823 B1 | 11/2002 | Michelson |
| 6,482,207 B1 | 11/2002 | Errico |
| 6,482,234 B1 | 11/2002 | Weber et al. |
| 6,488,710 B2 | 12/2002 | Besselink |
| 6,491,724 B1 | 12/2002 | Ferree |
| 6,500,180 B1 | 12/2002 | Foley et al. |
| 6,500,205 B1 | 12/2002 | Michelson |
| 6,500,206 B1 | 12/2002 | Bryan |
| 6,520,996 B1 | 2/2003 | Manasas et al. |
| 6,524,312 B2 | 2/2003 | Landry et al. |
| 6,527,803 B1 | 3/2003 | Crozet et al. |
| 6,533,817 B1 | 3/2003 | Norton et al. |
| 6,533,818 B1 | 3/2003 | Weber et al. |
| 6,537,320 B1 | 3/2003 | Michelson |
| 6,540,748 B2 | 4/2003 | Lombardo |
| 6,558,423 B1 | 5/2003 | Michelson |
| 6,558,424 B1 | 5/2003 | Thalgott |
| 6,562,040 B1 | 5/2003 | Wagner et al. |
| 6,562,074 B2 | 5/2003 | Gerbec et al. |
| 6,565,566 B1 | 5/2003 | Wagner et al. |
| 6,565,605 B2 | 5/2003 | Goble et al. |
| 6,569,442 B2 | 5/2003 | Gan et al. |
| 6,572,653 B1 | 6/2003 | Simonson |
| 6,576,016 B1 | 6/2003 | Hochschuler et al. |
| 6,579,318 B2 | 6/2003 | Varga et al. |
| 6,579,319 B2 | 6/2003 | Goble et al. |
| 6,582,467 B1 | 6/2003 | Teitelbaum et al. |
| 6,592,624 B1 | 7/2003 | Fraser et al. |
| 6,595,992 B1 | 7/2003 | Wagner et al. |
| 6,595,998 B2 | 7/2003 | Johnson et al. |
| 6,607,530 B1 | 8/2003 | Carl et al. |
| 6,610,091 B1 | 8/2003 | Reiley |
| 6,610,094 B2 | 8/2003 | Husson |
| 6,613,050 B1 | 9/2003 | Wagner et al. |
| 6,616,671 B2 | 9/2003 | Landry et al. |
| 6,626,904 B1 | 9/2003 | Jammet et al. |
| 6,626,905 B1 | 9/2003 | Schmeil et al. |
| 6,635,062 B2 | 10/2003 | Ray et al. |
| 6,641,614 B1 | 11/2003 | Wagner et al. |
| 6,648,893 B2 | 11/2003 | Dudasik |
| 6,648,915 B2 | 11/2003 | Sazy |
| 6,648,917 B2 | 11/2003 | Gerbec et al. |
| 6,666,870 B2 | 12/2003 | Dixon |
| 6,666,891 B2 | 12/2003 | Boehm et al. |
| 6,679,915 B1 | 1/2004 | Cauthen |
| 6,682,533 B1 | 1/2004 | Dinsdale et al. |
| 6,685,742 B1 | 2/2004 | Jackson |
| 6,692,495 B1 | 2/2004 | Zacouto |
| 6,706,070 B1 | 3/2004 | Wagner et al. |
| 6,712,819 B2 | 3/2004 | Zucherman et al. |
| 6,716,247 B2 | 4/2004 | Michelson |
| 6,719,796 B2 | 4/2004 | Cohen et al. |
| 6,733,531 B1 | 5/2004 | Trieu |
| 6,736,850 B2 | 5/2004 | Davis |
| 6,743,257 B2 | 6/2004 | Castro |
| 6,758,861 B2 | 7/2004 | Ralph et al. |
| 6,767,367 B1 | 7/2004 | Michelson |
| 6,770,096 B2 | 8/2004 | Bolger et al. |
| 6,773,460 B2 | 8/2004 | Jackson |
| 6,800,092 B1 | 10/2004 | Williams et al. |
| 6,802,844 B2 | 10/2004 | Ferree |
| 6,811,567 B2 | 11/2004 | Reiley |
| 6,821,298 B1 | 11/2004 | Jackson |
| 6,852,129 B2 | 2/2005 | Gerbec et al. |
| 6,863,673 B2 | 3/2005 | Gerbec et al. |
| 6,893,464 B2 | 5/2005 | Kiester |
| 6,896,680 B2 | 5/2005 | Michelson |
| 6,902,580 B2 | 6/2005 | Fallin et al. |
| 6,923,830 B2 | 8/2005 | Michelson |
| 6,928,284 B2 | 8/2005 | Palat et al. |
| 6,936,070 B1 | 8/2005 | Muhanna |
| 6,936,071 B1 | 8/2005 | Marnay et al. |
| 6,953,477 B2 | 10/2005 | Berry |
| 6,962,606 B2 | 11/2005 | Michelson |
| 6,964,664 B2 | 11/2005 | Freid et al. |
| 6,966,929 B2 | 11/2005 | Mitchell |
| 6,966,930 B2 | 11/2005 | Amin et al. |
| 6,974,478 B2 | 12/2005 | Reiley et al. |
| 6,981,975 B2 | 1/2006 | Michelson |
| 6,981,989 B1 | 1/2006 | Fleischmann et al. |
| 6,991,632 B2 | 1/2006 | Ritland |
| 6,994,727 B2 | 2/2006 | Khandkar et al. |
| 6,997,929 B2 | 2/2006 | Manzi et al. |
| 7,011,685 B2 | 3/2006 | Arnin et al. |
| 7,018,415 B1 | 3/2006 | McKay |

(56) References Cited

U.S. PATENT DOCUMENTS

| | | |
|---|---|---|
| 7,029,475 B2 | 4/2006 | Panjabi |
| 7,060,073 B2 | 6/2006 | Frey et al. |
| 7,060,100 B2 | 6/2006 | Ferree |
| 7,083,622 B2 | 8/2006 | Simonson |
| 7,083,649 B2 | 8/2006 | Zucherman et al. |
| 7,090,698 B2 | 8/2006 | Goble et al. |
| 7,101,398 B2 | 9/2006 | Dooris et al. |
| 7,112,206 B2 | 9/2006 | Michelson |
| 7,118,579 B2 | 10/2006 | Michelson |
| 7,118,580 B1 | 10/2006 | Beyersdorff et al. |
| 7,128,760 B2 | 10/2006 | Michelson |
| 7,147,664 B2 | 12/2006 | Louis et al. |
| 7,153,310 B2 | 12/2006 | Ralph et al. |
| 7,198,644 B2 | 4/2007 | Schultz et al. |
| 7,204,852 B2 | 4/2007 | Marnay et al. |
| 7,204,853 B2 | 4/2007 | Gordon et al. |
| 7,270,681 B2 | 9/2007 | Cauthen |
| 7,273,496 B2 | 9/2007 | Mitchell |
| 7,291,150 B2 | 11/2007 | Graf |
| 7,291,159 B2 | 11/2007 | Graf |
| 7,291,173 B2 | 11/2007 | Richelsoph et al. |
| 7,311,713 B2 | 12/2007 | Johnson et al. |
| 7,318,839 B2 | 1/2008 | Malberg et al. |
| 7,320,707 B2 | 1/2008 | Zucherman |
| 7,326,250 B2 | 2/2008 | Beaurain et al. |
| 7,338,525 B2 | 3/2008 | Ferree |
| 7,338,527 B2 | 3/2008 | Blatt et al. |
| 7,364,589 B2 | 4/2008 | Eisermann |
| 7,316,714 B2 | 8/2008 | Gordon et al. |
| 7,473,276 B2 | 1/2009 | Aebi et al. |
| 7,476,238 B2 | 1/2009 | Panjabi |
| 7,485,146 B1 | 2/2009 | Crook et al. |
| 7,517,359 B2 | 4/2009 | Drewry et al. |
| 7,547,309 B2 | 6/2009 | Bertagnoli et al. |
| 7,550,009 B2 | 6/2009 | Arnin et al. |
| 7,556,651 B2 | 7/2009 | Humphreys et al. |
| 7,575,580 B2 | 8/2009 | Lim et al. |
| 7,594,931 B2 | 9/2009 | Louis et al. |
| 7,594,932 B2 | 9/2009 | Aferzon et al. |
| 7,615,068 B2 | 11/2009 | Timm et al. |
| 7,635,379 B2 | 12/2009 | Callahan et al. |
| 7,682,396 B2 | 3/2010 | Beaurain et al. |
| 7,699,875 B2 | 4/2010 | Timm et al. |
| 7,708,778 B2 | 5/2010 | Gordon et al. |
| 7,713,287 B2 | 5/2010 | Timm et al. |
| 7,713,288 B2 | 5/2010 | Timm et al. |
| 7,727,280 B2 | 6/2010 | McLuen |
| 7,753,958 B2 | 7/2010 | Gordon et al. |
| 7,771,479 B2 | 8/2010 | Humphreys et al. |
| 7,785,351 B2 | 8/2010 | Gordon et al. |
| 7,794,480 B2 | 9/2010 | Gordon et al. |
| 7,799,082 B2 | 9/2010 | Gordon et al. |
| 7,811,309 B2 | 10/2010 | Timm et al. |
| 7,819,801 B2 | 10/2010 | Miles et al. |
| 7,828,849 B2 | 11/2010 | Lim |
| 7,846,188 B2 | 12/2010 | Moskowitz et al. |
| 7,896,919 B2 | 3/2011 | Belliard et al. |
| 7,909,869 B2 | 3/2011 | Gordon et al. |
| 7,909,877 B2 | 3/2011 | Krueger et al. |
| 7,927,374 B2 | 4/2011 | Duggal et al. |
| 7,931,675 B2 | 4/2011 | Panjabi et al. |
| 7,942,905 B2 | 5/2011 | Lim et al. |
| 7,951,170 B2 | 5/2011 | Jackson |
| 7,959,677 B2 | 6/2011 | Landry et al. |
| 8,043,379 B2 | 10/2011 | Moumene et al. |
| 8,052,723 B2 | 11/2011 | Gordon et al. |
| 8,062,375 B2 | 11/2011 | Glerum et al. |
| 8,080,062 B2 | 12/2011 | Armstrong et al. |
| 8,105,382 B2 | 1/2012 | Olmos et al. |
| 8,114,092 B2 | 2/2012 | Altarac et al. |
| 8,118,869 B2 | 2/2012 | Gordon et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,128,700 B2 | 3/2012 | Delurio et al. |
| 8,147,550 B2 | 4/2012 | Gordon et al. |
| 8,147,556 B2 | 4/2012 | Louis et al. |
| 8,157,844 B2 | 4/2012 | Gimbel et al. |
| 8,162,994 B2 | 4/2012 | Gimbel et al. |
| 8,172,903 B2 | 5/2012 | Gordon et al. |
| 8,182,514 B2 | 5/2012 | Gimbel et al. |
| 8,187,330 B2 | 5/2012 | Gimbel et al. |
| 8,257,440 B2 | 9/2012 | Gordon et al. |
| 8,257,443 B2 | 9/2012 | Kamran et al. |
| 8,267,965 B2 | 9/2012 | Gimbel et al. |
| 8,303,660 B1 | 11/2012 | Abdou |
| 8,313,528 B1 | 11/2012 | Wensel |
| 8,328,872 B2 | 12/2012 | Duffield et al. |
| 8,377,098 B2 | 2/2013 | Landry et al. |
| 8,388,687 B2 | 3/2013 | Gimbel et al. |
| 8,398,713 B2 | 3/2013 | Weiman |
| 8,414,652 B2 | 4/2013 | Moumene et al. |
| 8,435,298 B2 | 5/2013 | Weiman |
| 8,475,461 B2 | 7/2013 | Butler et al. |
| 8,486,148 B2 | 7/2013 | Butler et al. |
| 8,491,659 B2 | 7/2013 | Weiman |
| 8,512,407 B2 | 8/2013 | Butler et al. |
| 8,518,120 B2 | 8/2013 | Glerum et al. |
| 8,523,912 B2 | 9/2013 | Gimbel et al. |
| 8,545,563 B2 | 10/2013 | Brun et al. |
| 8,556,979 B2 | 10/2013 | Glerum et al. |
| 8,591,553 B2 | 11/2013 | Eisermann et al. |
| 8,597,358 B2 | 12/2013 | Landry et al. |
| 8,603,168 B2 | 12/2013 | Gordon et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,679,183 B2 | 3/2014 | Glerum et al. |
| 8,685,098 B2 | 4/2014 | Glerum et al. |
| 8,709,086 B2 | 4/2014 | Glerum |
| 8,753,398 B2 | 6/2014 | Gordon et al. |
| 8,940,022 B2 | 1/2015 | Landry et al. |
| 8,940,051 B2 | 1/2015 | Gimbel et al. |
| 9,039,774 B2 | 5/2015 | Chataigner et al. |
| 9,044,337 B2 | 6/2015 | Dinville et al. |
| 9,078,765 B2 | 7/2015 | Louis et al. |
| 9,173,745 B2 | 11/2015 | Dinville et al. |
| 2001/0020476 A1 | 9/2001 | Gan et al. |
| 2001/0032020 A1 | 10/2001 | Besselink |
| 2002/0040243 A1 | 4/2002 | Atalli et al. |
| 2002/0045945 A1 | 4/2002 | Liu et al. |
| 2002/0065557 A1 | 5/2002 | Goble et al. |
| 2002/0068977 A1 | 6/2002 | Jackson |
| 2002/0072801 A1 | 6/2002 | Michelson |
| 2002/0082701 A1 | 6/2002 | Zdeblick et al. |
| 2002/0091390 A1 | 7/2002 | Michelson |
| 2002/0095154 A1 | 7/2002 | Atkinson et al. |
| 2002/0123806 A1 | 9/2002 | Reiley |
| 2002/0128659 A1 | 9/2002 | Michelson |
| 2002/0128714 A1 | 9/2002 | Manasas et al. |
| 2002/0130112 A1 | 9/2002 | Manasas et al. |
| 2002/0138077 A1 | 9/2002 | Ferree |
| 2002/0143401 A1 | 10/2002 | Michelson |
| 2003/0028250 A1 | 2/2003 | Reiley et al. |
| 2003/0040802 A1 | 2/2003 | Errico |
| 2003/0055427 A1 | 3/2003 | Graf |
| 2003/0069643 A1 | 4/2003 | Ralph et al. |
| 2003/0074063 A1 | 4/2003 | Gerbec et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0074074 A1 | 4/2003 | Errico et al. |
| 2003/0135275 A1 | 7/2003 | Garcia et al. |
| 2003/0135277 A1 | 7/2003 | Bryan et al. |
| 2003/0139812 A1 | 7/2003 | Gacia et al. |
| 2003/0149483 A1 | 8/2003 | Michelson |
| 2003/0176923 A1 | 9/2003 | Keller et al. |
| 2003/0187436 A1 | 10/2003 | Bolger et al. |
| 2003/0191470 A1 | 10/2003 | Ritland |

(56) References Cited

U.S. PATENT DOCUMENTS

| | | |
|---|---|---|
| 2003/0204259 A1 | 10/2003 | Goble et al. |
| 2003/0204260 A1 | 10/2003 | Ferree |
| 2003/0220643 A1 | 11/2003 | Ferree |
| 2003/0225409 A1 | 12/2003 | Freid et al. |
| 2003/0233145 A1 | 12/2003 | Landry et al. |
| 2004/0006391 A1 | 1/2004 | Reiley |
| 2004/0010312 A1 | 1/2004 | Enayati |
| 2004/0019353 A1 | 1/2004 | Freid et al. |
| 2004/0030387 A1 | 2/2004 | Landry et al. |
| 2004/0030389 A1 | 2/2004 | Ferree |
| 2004/0039448 A1 | 2/2004 | Pisharodi |
| 2004/0044411 A1 | 3/2004 | Suddaby |
| 2004/0049190 A1 | 3/2004 | Biedermann et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049280 A1 | 3/2004 | Cauthen |
| 2004/0049281 A1 | 3/2004 | Reiley |
| 2004/0064136 A1 | 4/2004 | Papineau et al. |
| 2004/0087947 A1 | 5/2004 | Lim et al. |
| 2004/0093083 A1 | 5/2004 | Branch et al. |
| 2004/0102774 A1 | 5/2004 | Trieu |
| 2004/0106997 A1 | 6/2004 | Lieberson |
| 2004/0117020 A1 | 6/2004 | Frey et al. |
| 2004/0127989 A1 | 7/2004 | Dooris et al. |
| 2004/0133278 A1 | 7/2004 | Marino et al. |
| 2004/0133281 A1 | 7/2004 | Khandkar et al. |
| 2004/0138662 A1 | 7/2004 | Landry et al. |
| 2004/0138749 A1 | 7/2004 | Zucherman |
| 2004/0143265 A1 | 7/2004 | Landry et al. |
| 2004/0143332 A1 | 7/2004 | Krueger et al. |
| 2004/0147928 A1 | 7/2004 | Landry et al. |
| 2004/0153065 A1 | 8/2004 | Lim |
| 2004/0167626 A1 | 8/2004 | Geremakis et al. |
| 2004/0181223 A1 | 9/2004 | Ritland |
| 2004/0181284 A1 | 9/2004 | Simonson |
| 2004/0220567 A1 | 11/2004 | Eisermann et al. |
| 2004/0236327 A1 | 11/2004 | Paul et al. |
| 2004/0236329 A1 | 11/2004 | Panjabi |
| 2004/0243240 A1 | 12/2004 | Beaurain et al. |
| 2004/0254643 A1 | 12/2004 | Jackson |
| 2004/0254644 A1 | 12/2004 | Taylor |
| 2004/0267364 A1 | 12/2004 | Carli et al. |
| 2004/0267369 A1 | 12/2004 | Lyons et al. |
| 2005/0010295 A1 | 1/2005 | Michelson |
| 2005/0015146 A1 | 1/2005 | Louis et al. |
| 2005/0015149 A1 | 1/2005 | Michelson |
| 2005/0021144 A1 | 1/2005 | Malberg et al. |
| 2005/0027361 A1 | 2/2005 | Reiley |
| 2005/0027362 A1 | 2/2005 | Williams et al. |
| 2005/0033432 A1 | 2/2005 | Gordon et al. |
| 2005/0033437 A1 | 2/2005 | Bao et al. |
| 2005/0033439 A1 | 2/2005 | Gordon et al. |
| 2005/0043800 A1 | 2/2005 | Paul et al. |
| 2005/0060034 A1 | 3/2005 | Berry |
| 2005/0085815 A1 | 4/2005 | Harms et al. |
| 2005/0096745 A1 | 5/2005 | Lamons |
| 2005/0107881 A1 | 5/2005 | Neville et al. |
| 2005/0113927 A1 | 5/2005 | Malek |
| 2005/0124991 A1 | 6/2005 | Jahng |
| 2005/0125061 A1 | 6/2005 | Zucherman et al. |
| 2005/0125062 A1 | 6/2005 | Biedermann et al. |
| 2005/0131406 A1 | 6/2005 | Reiley |
| 2005/0131408 A1 | 6/2005 | Sicvol et al. |
| 2005/0143818 A1 | 6/2005 | Yuan et al. |
| 2005/0149020 A1 | 7/2005 | Jahng |
| 2005/0149023 A1 | 7/2005 | Ritland |
| 2005/0154461 A1 | 7/2005 | Humphreys et al. |
| 2005/0154462 A1 | 7/2005 | Zucherman et al. |
| 2005/0154465 A1 | 7/2005 | Hodges et al. |
| 2005/0154466 A1 | 7/2005 | Humphreys et al. |
| 2005/0159818 A1 | 7/2005 | Blain |
| 2005/0171543 A1 | 8/2005 | Timm et al. |
| 2005/0171608 A1 | 8/2005 | Peterman et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0182401 A1 | 8/2005 | Timm et al. |
| 2005/0182409 A1 | 8/2005 | Callahan et al. |
| 2005/0033431 A1 | 9/2005 | Gordon et al. |
| 2005/0203517 A1 | 9/2005 | Jahng et al. |
| 2005/0209697 A1 | 9/2005 | Paponneau et al. |
| 2005/0209698 A1 | 9/2005 | Gordon et al. |
| 2005/0222569 A1 | 10/2005 | Panjabi |
| 2005/0228500 A1 | 10/2005 | Kim et al. |
| 2005/0245930 A1 | 11/2005 | Timm et al. |
| 2005/0251261 A1 | 11/2005 | Peterman |
| 2005/0256578 A1 | 11/2005 | Blatt et al. |
| 2005/0261771 A1 | 11/2005 | Paul et al. |
| 2005/0117725 A1 | 12/2005 | Parson |
| 2005/0273167 A1 | 12/2005 | Triplett et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2005/0288670 A1 | 12/2005 | Panjabi et al. |
| 2006/0009768 A1 | 1/2006 | Ritland |
| 2006/0009850 A1 | 1/2006 | Frigg et al. |
| 2006/0015100 A1 | 1/2006 | Panjabi et al. |
| 2006/0149385 A1 | 1/2006 | McKay |
| 2006/0036240 A1 | 2/2006 | Colleran |
| 2006/0036245 A1 | 2/2006 | Stern |
| 2006/0084986 A1 | 4/2006 | Grinberg et al. |
| 2006/0084988 A1 | 4/2006 | Kim |
| 2006/0089717 A1 | 4/2006 | Krishna et al. |
| 2006/0095132 A1 | 5/2006 | Kirschman |
| 2006/0122701 A1 | 6/2006 | Kiester |
| 2006/0129244 A1 | 6/2006 | Ensign |
| 2006/0142759 A1 | 6/2006 | Amin et al. |
| 2006/0149228 A1 | 7/2006 | Schlapfer et al. |
| 2006/0149229 A1 | 7/2006 | Kwak et al. |
| 2006/0149278 A1 | 7/2006 | Abdou |
| 2006/0149372 A1 | 7/2006 | Paxson et al. |
| 2006/0149383 A1 | 7/2006 | Amin et al. |
| 2006/0155377 A1 | 7/2006 | Beaurain et al. |
| 2006/0167547 A1 | 7/2006 | Suddaby |
| 2006/0178745 A1 | 8/2006 | Bartish et al. |
| 2006/0178746 A1 | 8/2006 | Bartish et al. |
| 2006/0189983 A1 | 8/2006 | Fallin et al. |
| 2006/0195114 A1 | 8/2006 | Bertagnoli |
| 2006/0195191 A1 | 8/2006 | Sweeney et al. |
| 2006/0195192 A1 | 8/2006 | Gordon et al. |
| 2006/0217712 A1 | 9/2006 | Mueller et al. |
| 2006/0229729 A1 | 10/2006 | Gordon |
| 2006/0235426 A1 | 10/2006 | Lim et al. |
| 2006/0241642 A1 | 10/2006 | Amin et al. |
| 2006/0241769 A1 | 10/2006 | Gordon et al. |
| 2006/0241770 A1 | 10/2006 | Rhoda et al. |
| 2006/0241771 A1 | 10/2006 | Gordon et al. |
| 2006/0247635 A1 | 11/2006 | Gordon et al. |
| 2006/0247779 A1 | 11/2006 | Gordon et al. |
| 2006/0260483 A1 | 11/2006 | Hartmann et al. |
| 2006/0264937 A1 | 11/2006 | White |
| 2006/0265068 A1 | 11/2006 | Schwab |
| 2006/0265074 A1 | 11/2006 | Krishna |
| 2006/0265077 A1 | 11/2006 | Zwirkoski |
| 2007/0010886 A1 | 1/2007 | Banick |
| 2007/0073405 A1 | 3/2007 | Verhulst et al. |
| 2007/0073406 A1 | 3/2007 | Gordon et al. |
| 2007/0093828 A1 | 4/2007 | Abdou |
| 2007/0093846 A1 | 4/2007 | Frigg et al. |
| 2007/0162137 A1 | 7/2007 | Kloss et al. |

(56) References Cited

U.S. PATENT DOCUMENTS

| | | |
|---|---|---|
| 2007/0225814 A1 | 7/2007 | Atkinson |
| 2007/0213720 A1 | 9/2007 | Gordon et al. |
| 2007/0213737 A1 | 9/2007 | Schermerhorn et al. |
| 2007/0213821 A1 | 9/2007 | Kwak et al. |
| 2007/0239279 A1 | 10/2007 | Francis |
| 2007/0270814 A1 | 11/2007 | Lim et al. |
| 2007/0270838 A1 | 11/2007 | Bruneau et al. |
| 2007/0270972 A1 | 11/2007 | Gordon et al. |
| 2007/0288094 A1 | 12/2007 | Krishna et al. |
| 2008/0015702 A1 | 1/2008 | Lakin et al. |
| 2008/0021285 A1 | 1/2008 | Drzyzga et al. |
| 2008/0027547 A1 | 1/2008 | Yu et al. |
| 2008/0033562 A1 | 2/2008 | Krishna |
| 2008/0065079 A1 | 3/2008 | Bruneau et al. |
| 2008/0133013 A1 | 6/2008 | Duggal et al. |
| 2008/0161853 A1 | 7/2008 | Arnold et al. |
| 2008/0177310 A1 | 7/2008 | Reiley |
| 2008/0183204 A1 | 7/2008 | Greenhalgh et al. |
| 2008/0234732 A1 | 9/2008 | Landry et al. |
| 2008/0234740 A1 | 9/2008 | Landry et al. |
| 2008/0234741 A1 | 9/2008 | Landry et al. |
| 2008/0234764 A1 | 9/2008 | Landry et al. |
| 2008/0234823 A1 | 9/2008 | Landry et al. |
| 2008/0249628 A1 | 10/2008 | Altarac et al. |
| 2008/0300685 A1 | 12/2008 | Carls et al. |
| 2008/0306488 A1 | 12/2008 | Altarac et al. |
| 2008/0306489 A1 | 12/2008 | Altarac et al. |
| 2008/0306557 A1 | 12/2008 | Altarac et al. |
| 2008/0312692 A1 | 12/2008 | Brennan et al. |
| 2009/0005817 A1 | 1/2009 | Friedrich et al. |
| 2009/0076549 A1 | 3/2009 | Lim et al. |
| 2009/0093846 A1 | 4/2009 | Hestad |
| 2009/0105757 A1 | 4/2009 | Gimbel et al. |
| 2009/0105758 A1 | 4/2009 | Gimbel et al. |
| 2009/0105759 A1 | 4/2009 | Gimbel et al. |
| 2009/0105764 A1 | 4/2009 | Jackson |
| 2009/0105820 A1 | 4/2009 | Jackson |
| 2009/0105827 A1 | 4/2009 | Gimbel et al. |
| 2009/0105828 A1 | 4/2009 | Gimbel et al. |
| 2009/0105829 A1 | 4/2009 | Gimbel et al. |
| 2009/0143862 A1 | 6/2009 | Trieu |
| 2009/0177196 A1 | 7/2009 | Zlock et al. |
| 2009/0270870 A1 | 10/2009 | Zubok et al. |
| 2010/0030336 A1 | 2/2010 | Cope |
| 2010/0082109 A1 | 4/2010 | Greenhalgh et al. |
| 2010/0100138 A1 | 4/2010 | Reynolds et al. |
| 2010/0174317 A1 | 7/2010 | Timm et al. |
| 2010/0185289 A1* | 7/2010 | Kirwan ................ A61F 2/4455 623/17.11 |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0222819 A1 | 9/2010 | Timm et al. |
| 2010/0222884 A1 | 9/2010 | Greenhalgh |
| 2010/0292796 A1 | 11/2010 | Greenhalgh et al. |
| 2010/0298941 A1 | 11/2010 | Hes et al. |
| 2010/0331985 A1 | 12/2010 | Gordon et al. |
| 2011/0015742 A1 | 1/2011 | Hong |
| 2011/0178599 A1 | 7/2011 | Brett |
| 2011/0196428 A1 | 8/2011 | Panjabi et al. |
| 2011/0208311 A1 | 8/2011 | Janowski |
| 2011/0230971 A1 | 9/2011 | Donner et al. |
| 2011/0319997 A1 | 12/2011 | Glerum et al. |
| 2012/0035729 A1 | 2/2012 | Glerum et al. |
| 2012/0143254 A1 | 6/2012 | Gimbel et al. |
| 2012/0245689 A1 | 9/2012 | Gimbel et al. |
| 2012/0265309 A1 | 10/2012 | Glerum et al. |
| 2012/0310349 A1 | 12/2012 | Gordon et al. |
| 2013/0023994 A1 | 1/2013 | Glerum |
| 2013/0158667 A1 | 6/2013 | Tabor et al. |
| 2013/0158669 A1 | 6/2013 | Sungarian et al. |
| 2013/0245769 A1 | 9/2013 | Gimbel et al. |
| 2014/0067071 A1 | 3/2014 | Weiman et al. |
| 2015/0057754 A1 | 2/2015 | Reed et al. |
| 2016/0008142 A1 | 1/2016 | Louis et al. |

* cited by examiner

LIMITED PROFILE INTERVERTEBRAL IMPLANT WITH INCORPORATED FASTENING AND LOCKING MECHANISM

PRIORITY CLAIM

The present application is a continuation-in-part of U.S. patent application Ser. No. 14/260,869, filed Apr. 24, 2014, entitled "LIMITED PROFILE INTERVERTEBRAL IMPLANT WITH INCORPORATED FASTENING MECHANISM", all of which is incorporated herein by reference.

BACKGROUND OF THE INVENTION

1. Field of the Invention

The present disclosure generally relates to an intervertebral implant. More particularly, the disclosure generally relates to an intervertebral implant with an incorporated fastening mechanism including systems and methods for installing the intervertebral implant.

2. Description of the Relevant Art

The human spine is a complex mechanical structure including alternating bony vertebrae and fibrocartilaginous discs that are connected by strong ligaments and supported by musculature that extends from the skull to the pelvis and provides axial support to the body. The intervertebral discs provide mechanical cushion between adjacent vertebral segments of the spinal column and include three basic components: the nucleus pulposus, the annulus fibrosis, and two vertebral end plates. The end plates are made of thin cartilage overlying a thin layer of hard cortical bone that attaches to the spongy, cancellous bone of the vertebral body. The annulus fibrosis forms the disc's perimeter and is a tough outer ring that binds adjacent vertebrae together. The vertebrae generally include a vertebral foramen bounded by the anterior vertebral body and the neural arch, which consists of two pedicles and two laminae that are united posteriorly. The spinous and transverse processes protrude from the neural arch. The superior and inferior articular facets lie at the root of the transverse process.

The human spine is highly flexible, capable of a high degree of curvature and twist in nearly every direction. Genetic or developmental irregularities, trauma, chronic stress, and degeneration, however, can result in spinal pathologies for which surgical intervention may be necessary. A disc may become damaged or diseased, reducing intervertebral separation. Reduction of the intervertebral separation may reduce a height of the disc nucleus, which may cause the annulus to buckle in areas where the laminated plies are loosely bonded. As the overlapping laminated plies of the annulus begin to buckle and separate, circumferential or radial annular tears may occur. Such disruption to the natural intervertebral separation may produce pain, which may be alleviated by removal of the disc and subsequently maintaining the natural separation of the vertebrae. In cases of chronic back pain resulting from a degenerated or herniated disc, removal of the disc becomes medically necessary.

In some instances, a damaged disc may be replaced with a disc prosthesis intended to duplicate the dynamic function of a natural spinal disc. In other cases, it may be desirable to fuse adjacent vertebrae of a human spine together after removal of a disc. This procedure is generally referred to as "intervertebral fusion" or "interbody fusion." Intervertebral fusion has been accomplished with a variety of techniques and instruments. In some instances intervertebral fusion has been accomplished by placing structural bone or interbody fusion cage implants filled with bone graft material (e.g., morselized bone) within an intervertebral space where the spinal disc once resided. Fusion cage implants have been generally successful in promoting fusion and maintaining suitable disc height. Insertion of fusion cage implants, however, may be difficult. For example, fusion cages inserted from a posterior approach are generally limited in size by the space between the nerve roots which the implant is moved through during insertion. Moreover, as the distance between vertebral end plates is reduced, the height of the intervertebral space is reduced, thereby limited the size of implants introduced into the space, and often requiring distraction (e.g., spreading of the vertebrae) to achieve a suitable separation of the vertebrae.

Intervertebral fusion implants are typically inserted between adjacent vertebrae. Fasteners are typically deployed to couple the implant to one or more of the adjacent vertebrae. Problems occur due to the angle at which fasteners need to be employed through the implant into the adjacent vertebra relative to the patient's body. Fastener insertion instruments frequently interfere with a patient's body (e.g., chest, chin, etc.) due to the obtuse angles at which the instrument must be used relative to the implant and spine. These angles may make it difficult for the instrument to engage the fastener and/or apply sufficient pressure/force to the fastener using the instrument (e.g., especially when C2-C3 or C6-C7 levels are fused). It should be noted that fasteners which are positioned substantially perpendicular to vertebrae endplates provide better resistance to pull-out.

Accordingly, there is a desire to provide an implant technique that provides a simple and reliable solution for intervertebral fusion wherein fasteners are inserted substantially perpendicular to an endplate of a vertebra.

SUMMARY

In some embodiments, a spinal implant may include little to no profile extending beyond the vertebrae the implant is positioned between during use. In some embodiments, the implant may include at least one coupling mechanisms (in some embodiments, there may be at least two coupling mechanisms) incorporated into a preassembled implant. The coupling mechanism may function to couple the implant to the two vertebrae the implant is positioned between. The coupling mechanism may include an elongated member positionable in an opening in the implant, the elongated member may be inhibited from being removed from the opening. A first end of a fastening member may be coupled to the elongated member such that the fastening member is allowed to move relative to the elongated member. The fastening member may be curved. The coupling member may be activated, during use, by moving the elongated member from a first position to a second position. The first position may include a first end of the elongated member extending out from a first face of the implant and the second position may include the first end of the elongated member inserted in the implant such that the first end is substantially aligned with the first face. When the elongated member is moved from the first position to the second position a second end of the fastening member may be conveyed out of a channel in the implant wherein the opening extends out of a side of the implant adjacent to a vertebra during use. The second end of the fastening member may extend, during use, in the adjacent vertebra coupling the implant to the vertebrae.

In some embodiments, an intervertebral implant may include a body including a superior surface and an inferior surface. At least a portion of the superior surface may function to contact an endplate of an upper adjacent vertebra during use. The inferior surface may function to contact an endplate of a lower adjacent vertebra during use. The implant may include a first and a second channel extending from an anterior end to a posterior end of the body. The first and the second channels may be positioned on substantially opposing sides of the body. The implant may include a first and a second anchor channel. In some embodiments, an anchor channel may be curved. A first end of the first anchor channel may be coupled to the first channel adjacent the anterior end and a second end of the first anchor channel extends through the superior face of the body. A first end of the second anchor channel may be coupled to the second channel adjacent the anterior end and a second end of the second anchor channel extends through the inferior face of the body.

The implant may include a first and a second guide member positionable respectively in the first and the second channels. The guide members may be movable from a first position, a first end of the guide member extending from the anterior end of the body, to a second position, the first end of the guide member substantially flush with the anterior end of the body, during use. The implant may include a first and a second anchor coupled to the first end of the first and the second guide members respectively. When the first guide member moves from the first position to the second position the first anchor may be conveyed through the first anchor channel and couple the body to the upper adjacent vertebra during use. When the second guide member moves from the first position to the second position the second anchor may be conveyed through the second anchor channel and couple the body to the lower adjacent vertebra during use.

In some embodiments, substantially all of an outer perimeter of the body of the implant may be positioned within the outer perimeter of the upper and lower adjacent vertebrae after installation.

In some embodiments, the first guide member may include a coupling member adjacent the first end of the guide member. The first anchor may include an opening into which the coupling member is positionable. The coupling member may include a post.

In some embodiments, the body may include an opening extending from the superior surface to the inferior surface. The opening may hold biological material during use.

In some embodiments, the anterior end comprises an opening. The opening may function to couple to an insertion instrument.

In some embodiments, the implant may include a first locking mechanism which inhibits, during use, the first guide member from moving from the second position to the first position upon activation of the first locking mechanism. In some embodiments, the first locking mechanism may include a locking member and a resilient member. The resilient member may bias the locking member in a locked position.

In some embodiments, an anchor may include a plurality of ridges along at least one edge of the anchor. At least some of the plurality of ridges may be oriented in a direction substantially opposing to a direction of insertion of the first anchor in the adjacent vertebra during use.

In some embodiments, the first guide member may include an at least partially flexible second member. The second member may be positioned towards a distal end (e.g., posterior end) of the first guide member. The second member may flex toward the first guide member when force is applied to the second member. In some embodiments, the second member may include an engager. The engager may be positioned on a side of the second member opposite to the first guide member. The engager may interact, during use, with a first surface feature to inhibit movement of the first guide member in the first channel. The engager may interact, during use, with a first surface feature to inhibit movement of the first guide member in the first channel from the first position to the second position. The engager may interact, during use, with a first and/or a second surface feature to inhibit movement of the first guide member in the first channel. The engager may interact, during use, with a second surface feature to inhibit movement of the first guide member in the first channel from the second position to the first position.

In some embodiments, the first guide member may include a second member. The second member may be positioned coupled towards a distal end (e.g., posterior end) of the first guide member. In some embodiments, the second member may include an engager. The engager may interact, during use, with a first feature to inhibit movement of the first guide member in the first channel. The engager may interact, during use, with a first feature to inhibit movement of the first guide member in the first channel from the first position to the second position. The engager may interact, during use, with a first and/or a second surface feature to inhibit movement of the first guide member in the first channel. The engager may interact, during use, with a second surface feature to inhibit movement of the first guide member in the first channel from the second position to the first position.

In some embodiments, the first guide member may include a stop. The stop may be positioned towards a distal end of the first guide member and proximal to the second member. The stop may interact, during use, with a second feature to inhibit movement of the first guide member in the first channel. The stop may interact, during use, with a second feature to inhibit movement of the first guide member in the first channel from the first position to the second position. In some embodiments, the first and/or second feature may include an elongated member positioned at least partially in the first channel.

In some embodiments, the implant may include a first stop which functions to inhibit extraction of the first guide member from the first channel at the anterior end. The first stop may include a first pin.

In some embodiments, the implant may include a second stop positioned towards the anterior end of the body. The second stop may function to inhibit movement of the first guide member in the first channel. The second stop may function to inhibit movement of the first guide member in the first channel from the first position to the second position.

In some embodiments, the implant may include a third stop positioned towards the posterior end of the body. The third stop may function to inhibit movement of the first guide member in the first channel. The third stop may function to inhibit movement of the first guide member in the first channel from the second position to the first position.

In some embodiments, the implant may include a plurality of surface deformations positioned on the inferior surface and/or the superior surface. Surface deformations may include protrusions.

In some embodiments, a method may include implanting an intervertebral implant within an intervertebral space between endplates of adjacent vertebra. The method may include implanting an intervertebral implant between an upper adjacent vertebra and a lower adjacent vertebra such that a superior surface of a body of the intervertebral implant contacts an endplate of the upper adjacent vertebra and an inferior surface of the body contacts an endplate of the lower adjacent vertebra. The method may include conveying a first guide member through a first channel from a first position, a first end of the first guide member extending from an anterior end of the body, to a second position, the first end of the first guide member substantially flush with the anterior end of the body, during use. The method may include conveying a first anchor through a first anchor channel when the first guide member moves from the first position to the second position. A first end of the first anchor channel may be coupled to the first channel adjacent the anterior end and a second end of the first anchor channel extends through the superior face of the body. The method may include coupling the body to the upper adjacent vertebra using the first anchor.

In some embodiments, an intervertebral implant system may include an intervertebral implant and an anchor insertion instrument. In some embodiments, the intervertebral implant may include a body comprising a superior surface and an inferior surface. At least a portion of the superior surface may function to contact an endplate of an upper adjacent vertebra during use. The inferior surface may function to contact an endplate of a lower adjacent vertebra during use. The intervertebral implant may include a first anchor channel. A first end of the first anchor channel may be coupled to the anterior end and a second end of the first anchor channel extends through the inferior or superior face of the body. The intervertebral implant may include a first anchor positionable in the first anchor channel. The first anchor may include a first end and a second end. The first end may include a tapered end. The second end may include an elongated slot coupled to an expanded opening including a first dimension. The elongated slot comprises a first height and a first width. The first height may be greater than the first width.

In some embodiments, the anchor insertion instrument may include an elongated conduit. The anchor insertion instrument may include an elongated shaft positioned in the elongated conduit. The elongated shaft may be movable within the elongated conduit from a first position to a second position. The anchor insertion instrument may include a coupling member coupled to a distal end of the elongated shaft. The coupling member may include a second height and a second width. The second height may be greater than the second width. The second height may be less than the first height and the second height may be greater than the first width. The first dimension may be greater than the second height.

In some embodiments, a method may include implanting an intervertebral implant within an intervertebral space between endplates of adjacent vertebra. The method may include implanting an intervertebral implant between an upper adjacent vertebra and a lower adjacent vertebra such that a superior surface of a body of the intervertebral implant contacts an endplate of the upper adjacent vertebra and an inferior surface of the body contacts an endplate of the lower adjacent vertebra. The method may include inserting a coupling member of an anchor insertion instrument through an elongated slot and into an expanded opening coupled to the elongated slot in a second end of a first anchor, wherein the first anchor comprises a first end. The method may include rotating the coupling member within the expanded opening such that the coupling member is inhibited from extraction through the elongated slot of the first anchor. The method may include retracting an elongated shaft coupled, positionable in an elongated conduit, to the coupling member such that the second end of the first anchor abuts a distal end of the elongated conduit. The method may include conveying the first anchor through a first anchor channel in a body of the implant using the anchor insertion instrument. A first end of the first anchor channel may be coupled to the anterior end and a second end of the first anchor channel extends through the inferior or the superior face of the body. The method may include coupling the body to the upper or the lower adjacent vertebra using the first anchor.

In some embodiments, the method may include allowing articulation of the first anchor relative to the insertion instrument when the second end of the first anchor abuts a distal end of the elongated conduit. The second end of the first anchor may be substantially spherical. The distal end of the elongated conduit may be substantially concave.

BRIEF DESCRIPTION OF THE DRAWINGS

Advantages of the present invention may become apparent to those skilled in the art with the benefit of the following detailed description of the preferred embodiments and upon reference to the accompanying drawings.

Figure 1:
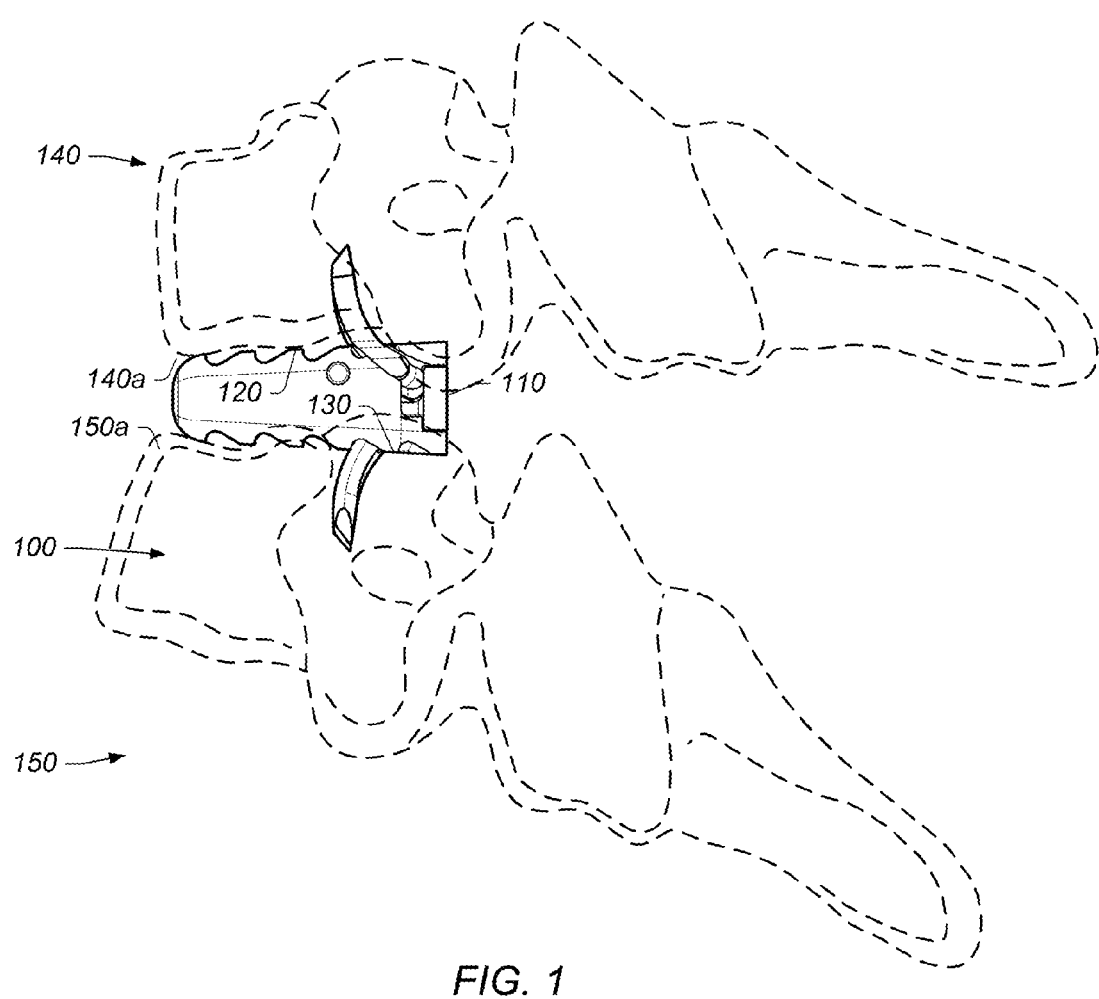
FIG. 1 depicts a diagram of a side view of an embodiment of a spinal implant positioned between two vertebrae.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third die electrically connected to the module substrate" does not preclude scenarios in which a "fourth die electrically connected to the module substrate" is connected prior to the third die, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task (e.g., a set of electrical conductors may be configured to electrically connect a module to another module, even when the two modules are not connected). In some contexts, "configured to" may be a broad recitation of structure generally meaning "having circuitry that" performs the task or tasks during operation. As such, the component can be configured to perform the task even when the component is not currently on. In general, the circuitry that forms the structure corresponding to "configured to" may include hardware circuits.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112 paragraph (f), interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The term "intervertebral" as used herein generally refers to an area between adjacent vertebrae in the vertebral column. In some embodiments, intervertebral as used herein includes the area between the sacrum and the pelvis (or the sacroiliac joint).

The term "vertebral column" as used herein generally refers to the 24 articulating vertebrae, and nine fused vertebrae in the sacrum and the coccyx. It is situated in the dorsal aspect of the torso, separated by intervertebral discs. The column houses and protects the spinal cord in its spinal canal, and is commonly called the spine or backbone. In some embodiments, vertebral column as used herein includes the sacroiliac joint connecting the sacrum and the pelvis.

Intervertebral Implant Embodiments:

In some embodiments, an intervertebral implant 100 may include a body 110 including a superior surface 120 and an inferior surface 130. FIG. 1 depicts a diagram of a side view of an embodiment of a spinal implant positioned between two vertebrae. At least a portion of the superior surface may function to contact an endplate 140a of an upper adjacent vertebra 140 during use. The inferior surface may function to contact an endplate 150a of a lower adjacent vertebra 150 during use.

Figure 2A:
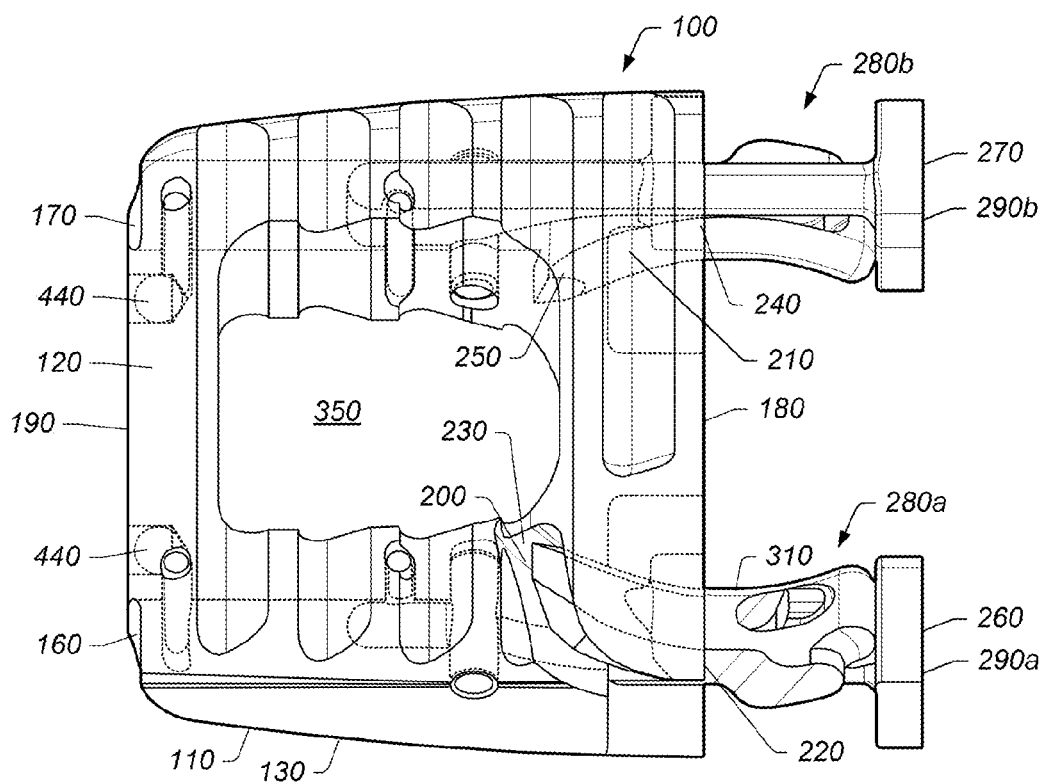
FIGS. 2A-B depict diagrams of a perspective view of an embodiment of a spinal implant with anchors in an unengaged position.
Figure 2B:
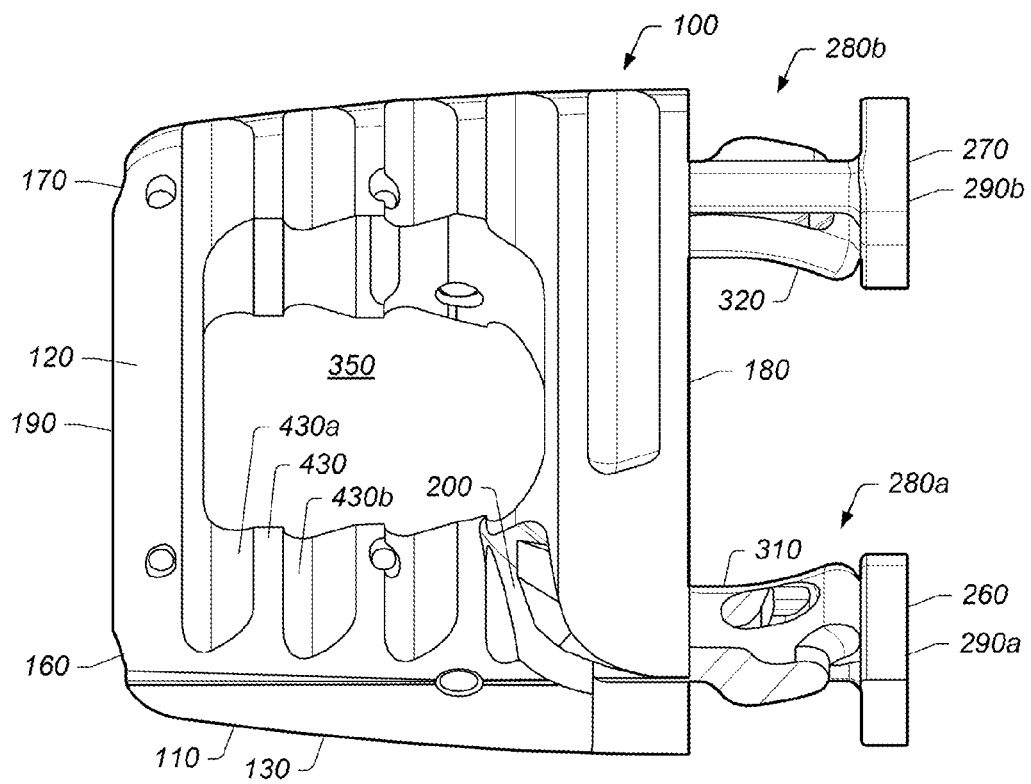
Figure 10:
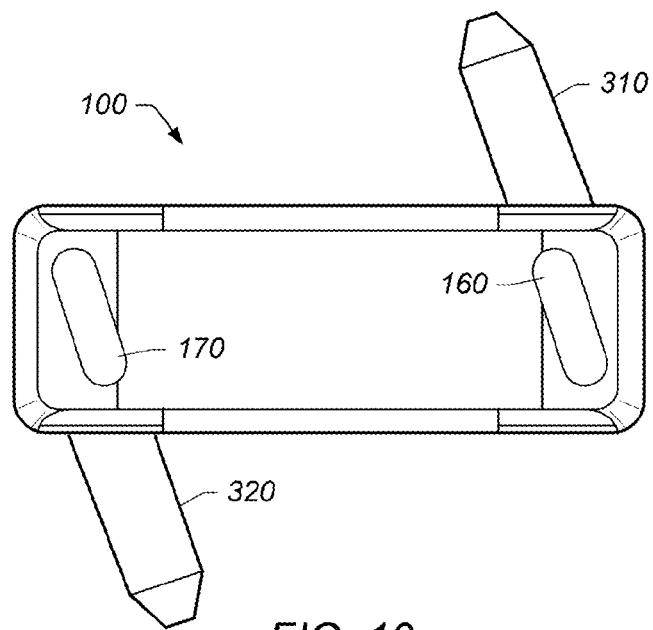
FIG. 10 depicts a diagram of an end view of an embodiment of an posterior end of a spinal implant with anchors in an engaged position.

FIGS. 2A-B depict diagrams of a perspective view of an embodiment of a spinal implant with anchors in an unengaged position. The implant may include a first 160 and a second channel 170 extending from an anterior end 180 to a posterior end 190 (e.g., depicted in FIG. 10) of the body 110. The first and the second channels may be positioned on substantially opposing sides of the body. The implant may include a first 200 and a second anchor channel 210. A first end 220 of the first anchor channel 200 may be coupled to the first channel 160 adjacent the anterior end 180 and a second end 230 of the first anchor channel may extend through the superior surface 120 of the body 110. A first end 240 of the second anchor channel 210 may be coupled to the second channel 170 adjacent the anterior end 180 and a second end 250 of the second anchor channel extends through the inferior surface 130 of the body 110.

The implant may include a first 260 and a second guide member 270 positionable respectively in the first 160 and the second channels 170. The guide members may be movable from a first position 280a-b, first ends 290a-b of the guide members extending from the anterior end of the body (e.g., depicted in FIGS. 2-3), to (e.g., the transition between the first and second positions depicted in FIG. 4) a second position 300a-b, the first ends 290a-b of the guide members substantially flush with the anterior end of the body (e.g., depicted in FIGS. 5 and 9), during use. In some embodiments, the first end 290 may function to inhibit movement of the guide member toward the posterior end. The first end 290 may function to inhibit movement of the guide member toward the posterior end due to interference of the first end with the anterior end (e.g., the first end is larger than the channels through which the guide members move). In some embodiments, guide members may include a shape which is complementary to a shape of the channels. Complementary shapes may function to inhibit movement of the guide members in the channels.

Figure 3:
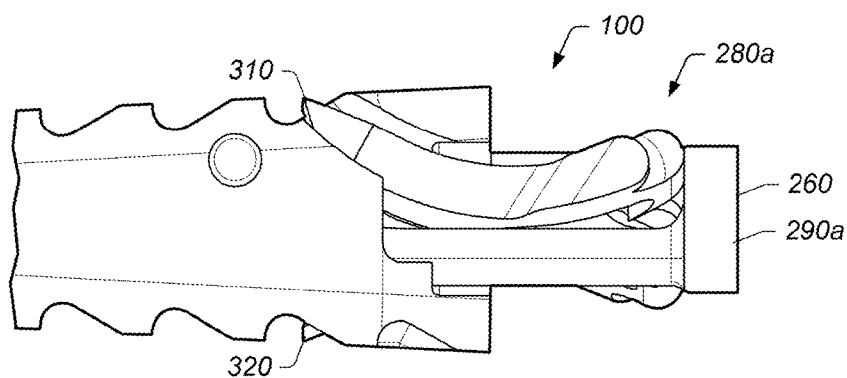
FIG. 3 depicts a diagram of a side view of an embodiment of a spinal implant with anchors in an unengaged position.
Figure 4:
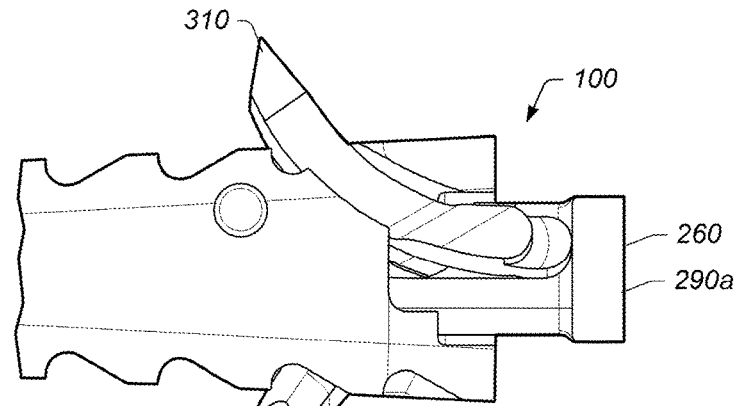
FIG. 4 depicts a diagram of a side view of an embodiment of a spinal implant with anchors in a partially engaged position.
Figure 5:
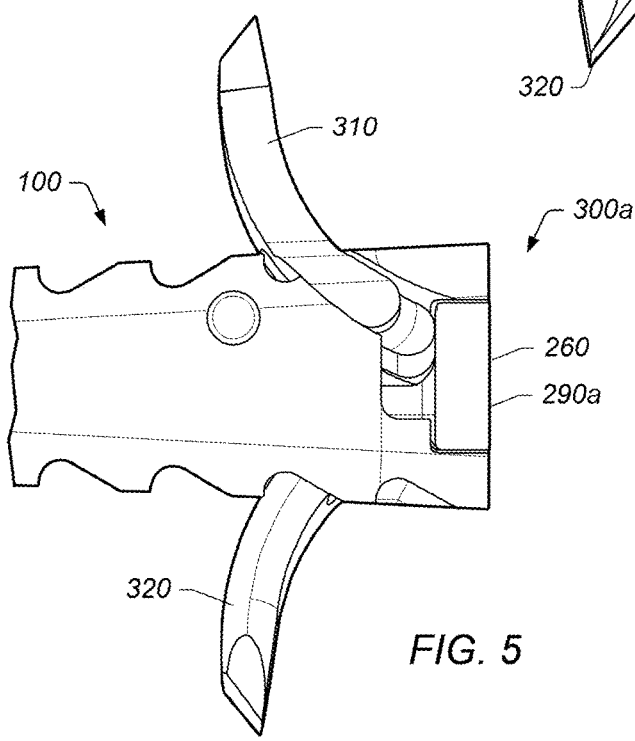
FIG. 5 depicts a diagram of a side view of an embodiment of a spinal implant with anchors in an engaged position.

The implant may include a first 310 and a second anchor 320 coupled adjacently to the first ends 290a-b of the first 260 and the second guide members 270 respectively. When the first guide member moves from the first position (e.g., depicted in FIGS. 2-3) to the second position (e.g., depicted in FIGS. 5 and 9) the first anchor may be conveyed through the first anchor channel and couple the body to the upper adjacent vertebra during use. When the second guide member moves from the first position to the second position the second anchor may be conveyed through the second anchor channel and couple the body to the lower adjacent vertebra during use. FIG. 3 depicts a diagram of a side view of an embodiment of the spinal implant 100 with anchors in an unengaged position. FIG. 4 depicts a diagram of a side view of an embodiment of the spinal implant 100 with anchors in a partially engaged position. FIG. 5 depicts a diagram of a side view of an embodiment of the spinal implant 100 with anchors in an engaged position. In some embodiments, anchors may include a shape which is complementary to a shape of the anchor channels. Complementary shapes may function to inhibit movement of the anchors in the anchor channels.

The anchors may be coupled to the guide members in a number of manners. The anchors may be coupled to the guide members such that the anchors are positionable relative to the guide members. The anchors may be coupled to the guide members such that the anchors may be conveyed through the anchor channel in a direction away from the guide members (e.g., such that the coupling point is not exposed to undue stress especially depending upon the materials the implant is formed from). In some embodiments, the anchors may be coupled to the guide members such that they are not directly attached but are inhibited from decoupling from one another. In some embodiments, the anchors may be coupled to the guide members such that they are directly attached and are inhibited from decoupling from one another.

In some embodiments, when the first guide member is in the first position with the anchors in an unengaged position a distal end of the anchor may be positioned in the anchor channel. Positioning of the distal end of the anchor in the anchor channel in combination with the coupling mechanism which couples the anchors to the guide members to inhibit disengagement of an anchor from a guide member.

Figure 7A:
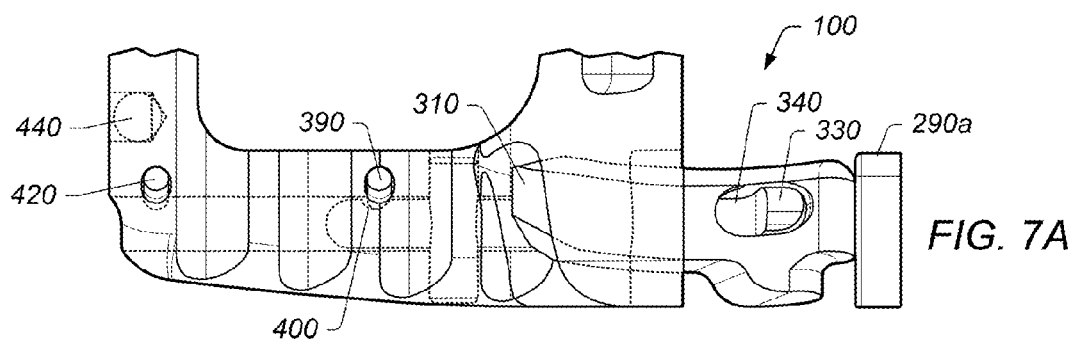
FIGS. 7A-B depict a diagram of a top view of embodiments of a portion of a spinal implant with anchors in an unengaged position wherein the body is depicted as substantially transparent.
Figure 7B:
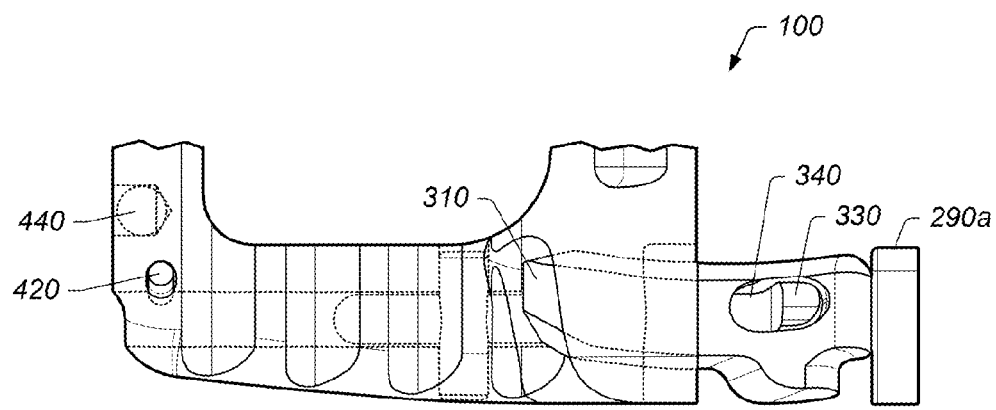
Figure 8:
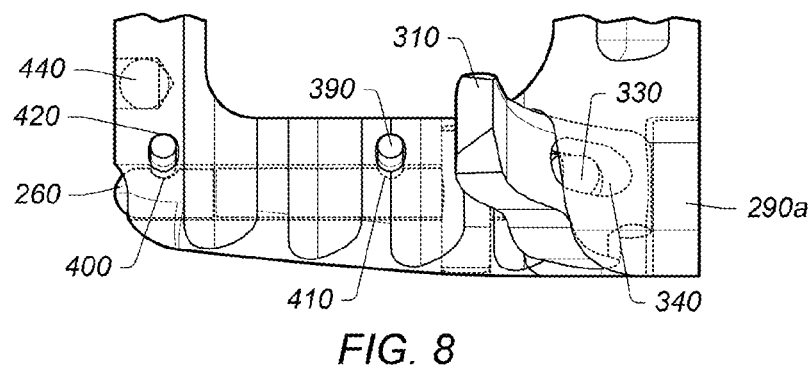
FIG. 8 depicts a diagram of a top view of an embodiment of a portion of a spinal implant with anchors in an engaged position wherein the body is depicted as substantially transparent.

In some embodiments, the first guide member 260 may include a coupling member 330 adjacent the first end 290a of the guide member (e.g., depicted in FIGS. 7-8). The first anchor may include an opening 340 into which the coupling member is positionable (e.g., depicted in FIGS. 7-8). The coupling member may include a post. The opening may be sized relative to the post to allow movement of the anchor relative to the guide member.

In some embodiments, substantially all of an outer perimeter of the body of the implant may be positioned within the outer perimeter of the upper and lower adjacent vertebrae after installation (e.g., depicted in FIG. 1).

In some embodiments, the body may include an opening 350 extending from the superior surface to the inferior surface (e.g., depicted in FIGS. 2A-B). The opening may hold biological material during use. In some embodiments, opening 350 may be filled with a substance/material to facilitate bone growth/fusion. Once implant 100 is implanted, the opening may facilitate a column of bone growth between the adjacent vertebrae through the opening 350. In some embodiments, an opening (e.g., opening 350) may function as a graft window containing bone chips and/or materials which facilitate tissue (e.g., bone) growth.

In some embodiments, the implant 100 may include only one anchor. The implant may include only one guide member and anchor combination. The implant may include one or more openings extending from the superior surface to the inferior surface for holding biological material. The anchor may be substantially centered in the body of the implant allowing biological material openings on either side of the anchor.

Figure 6A:
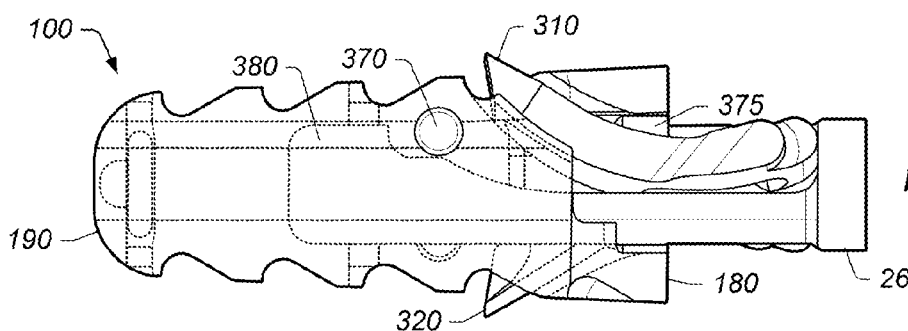
FIGS. 6A-C depict diagrams of a side view of several embodiments of a spinal implant with anchors in an unengaged position wherein the body is depicted as substantially transparent.
Figure 6B:
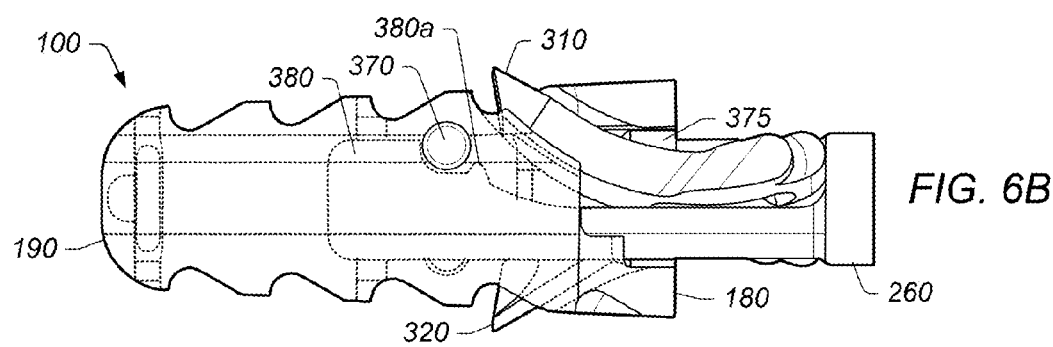
Figure 6C:
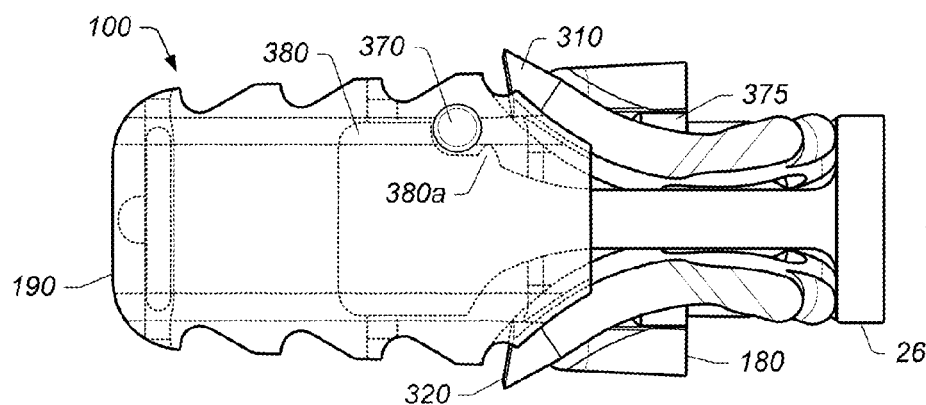

In some embodiments, the implant 100 may include two anchors coupled to a single guide member (e.g., as depicted in FIG. 6C). The first anchor may be coupled to an upper portion of a guide member and the second anchor may be coupled to an opposing lower portion of the guide member. As the guide member is advanced the anchors may penetrate the endplates of adjacent vertebrae, such that the first anchor couples the implant to the superior vertebra and the second anchor couples the implant to the inferior vertebra. Such an embodiment may require an implant with an increased thickness to accommodate such a double anchor configuration. Although the embodiment in FIG. 6C depicts the anchors as being positioned on one side of the implant, the anchors may be positioned in a more central location when there is only one guide member (e.g., with one or more openings on either one or both sides of the guide member through the body for organic material).

Figure 9:
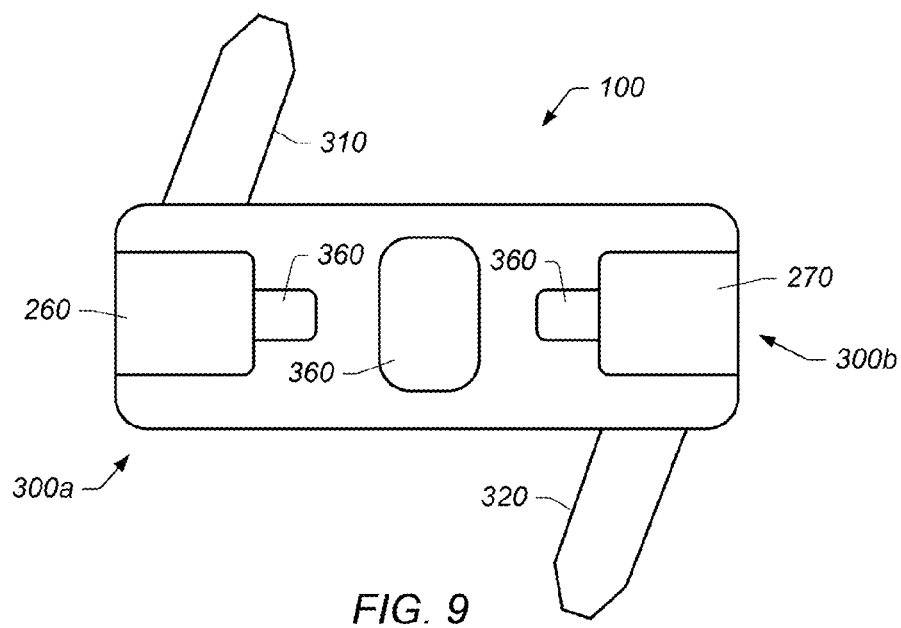
FIG. 9 depicts a diagram of an end view of an embodiment of an anterior end of a spinal implant with anchors in an engaged position.

In some embodiments, the anterior end may include a coupling mechanism 360. The coupling mechanism may function to couple to an insertion instrument. The coupling mechanism may include an opening. The opening may include an opening with a complementary shape to a portion of an insertion instrument. The opening may form a friction fit with the portion of the insertion instrument. In some embodiments, the coupling mechanism may include multiple openings (e.g., three openings as depicted in FIG. 9).

In some embodiments, the implant 100 may include a first stop 370 which functions to inhibit extraction of the first guide member 260 from the first channel 160 at the anterior end 180 (e.g., depicted in FIG. 6A-B). The first stop 370 may include a first pin. The first stop may include a first pin positioned horizontally. The first guide member 260 may include a second end 380 shaped such that the second end is inhibited from moving past the first stop when the first guide member moves toward the anterior end 180. Portions of the first guide member adjacent the first end 290a may be shaped such that the portions of the first guide member may move past the first stop allowing the first guide member to move towards the posterior end 190.

In some embodiments, the second end 380 of the first guide member 260 may include a portion 380a shaped such that the second end is inhibited from moving past the first stop when the first guide member moves toward the posterior end 190 (e.g., depicted in FIG. 6B). The first stop may function to inhibit movement of the first guide member in the first channel. The first stop and the second end may function to inhibit activation of the anchors until desired by a user.

In some embodiments, the first ends 290a-b of the guide members may be shaped such that the first end is inhibited from moving beyond the anterior end 180 of the body 110 inhibiting movement of the first guide member towards the posterior end 190. The first end of the guide members may fit within a recess 375 of the anterior end and as such be shaped to fit substantially flush with the anterior end (e.g., depicted in FIGS. 6 and 9). The first stop 370 and the first end may function to limit movement of the first guide member within a specified range.

In some embodiments, the implant may include a second stop 390 positioned towards the anterior end of the body. The second stop may function to inhibit movement of the first guide member in the first channel. The second stop may function to inhibit movement of the first guide member in the first channel from the first position to the second position. In some embodiments, the second stop may function to inhibit movement of the first guide member in the first channel from the second position to the first position. The second stop may include a second pin. The second pin may be positioned vertically. The second stop may interact with a first recess 400 in a side of a distal end of the first guide member (e.g., depicted in FIG. 7A). The second stop and the first recess may form a friction fit to inhibit movement of the first guide member when the first guide member is in the first position (i.e., when the anchors are in an unengaged position). The second stop and the first recess may function inhibit activation of the anchors until desired by a user.

As the first guide member moves toward the posterior end of the body of the implant, the second stop 390 may interact with a second recess 410 in a side of a proximal end of the first guide member (e.g., depicted in FIG. 8). The second stop and the second recess may form a friction fit to inhibit movement of the first guide member when the first guide member is in the second position (i.e., when the anchors are in an engaged position).

In some embodiments, the implant may include a third stop 420 positioned towards the posterior end of the body. The third stop may function to inhibit movement of the first guide member in the first channel. The third stop may function to inhibit movement of the first guide member in the first channel from the second position to the first position. In some embodiments, the third stop may function to inhibit movement of the first guide member in the first channel from the first position to the second position. The third stop may include a third pin. The third pin may be positioned vertically. The third stop may interact with the first recess 400 in a side of the distal end of the first guide member (e.g., depicted in FIG. 8). The third stop and the first recess may form a friction fit to inhibit movement of the first guide member when the first guide member is in the second position (i.e., when the anchors are in an engaged position).

In some embodiments, the implant may include all of the features described herein (at least those which do not interfere with one another). In some embodiments, the implant may include only some of the features described herein (e.g., the implant may not include second stop 390 as depicted in FIG. 7B). In some embodiments, stops may function as more of a hard stop or a soft stop. For example, stop 370 may function as a hard stop as far as far as inhibiting extraction of a guide member. To overcome or move past a hard stop may require disassembling and/or damaging at least a portion of the implant. The first end 290 may function as a hard stop to inhibit movement of the guide member toward the posterior end. While stop 370 may function as a soft stop as far as inhibiting movement of a portion of a guide member past the first stop during insertion of the guide member into a channel in the implant (e.g., as depicted in FIGS. 6B-C). A soft stop may function to only provide resistance to movement of a portion of the implant during normal operation of the implant during use.

Superior and/or inferior surfaces of the implant may include various features to facilitate engagement of the surfaces with endplates of adjacent vertebrae. In some embodiments, the implant may include a plurality of surface deformations positioned on the inferior surface and/or the superior surface. Surface deformations may include protrusions. For example (e.g., depicted in FIG. 2B) superior surface of body 110 may include protrusions (e.g., teeth) 430 extending there from. During use, teeth 430 may extend/penetrate into adjacent boney structure of the upper and lower adjacent vertebrae. Such penetration may help to fix a position of body 110, and, thus implant 100, relative to the vertebrae. Fixing or otherwise stabilizing the implant may reduce the likelihood of implant 100 being expelled from within the intervertebral space, and may promote bone attachment to and through implant 100.

In some embodiments, protrusions 430 may include unidirectional teeth that facilitate forward insertion of the members, but inhibit back-out of the members. For example, in the illustrated embodiment, teeth 430 include a ramped leading surface 430a and a substantially vertical trailing edge 430b (e.g., depicted in FIG. 2B). Thus, forward advancement of the members may be facilitated as boney structure of the vertebrae slides over ramped leading surface 430a of teeth 430 and backward advancement may be inhibited by substantially vertical trailing edge 430b hooking into or otherwise engaging the boney structure of the vertebrae.

In some embodiments, one or more portions of the implant 100 may include markers 440 (e.g., depicted in FIGS. 2A and 7-8). Markers may be used to assess a position of one or more portions of the implant during implantation in a subject. A portion of the implant may include none, one or multiple markers. Markers may provide radiographic opacity. Markers may be biocompatible. Markers may be of any size or shape. In some embodiments, a system may have multiple markers with different shapes in order to more easily identify different portions of the system and/or an orientation of one or more portions of the implant. In some embodiments, one or more markers may be formed from gold or tantalum.

In some embodiments, a method may include implanting an intervertebral implant within an intervertebral space between endplates of adjacent vertebra. The method may include implanting an intervertebral implant between an upper adjacent vertebra and a lower adjacent vertebra such that a superior surface of a body of the intervertebral implant contacts an endplate of the upper adjacent vertebra and an inferior surface of the body contacts an endplate of the lower adjacent vertebra. The method may include conveying a first guide member through a first channel from a first position, a first end of the first guide member extending from an anterior end of the body, to a second position, the first end of the first guide member substantially flush with the anterior end of the body, during use. The method may include conveying a first anchor through a first anchor channel when the first guide member moves from the first position to the second position. A first end of the first anchor channel may be coupled to the first channel adjacent the anterior end and a second end of the first anchor channel extends through the superior face of the body. The method may include coupling the body to the upper adjacent vertebra using the first anchor.

Figure 11:
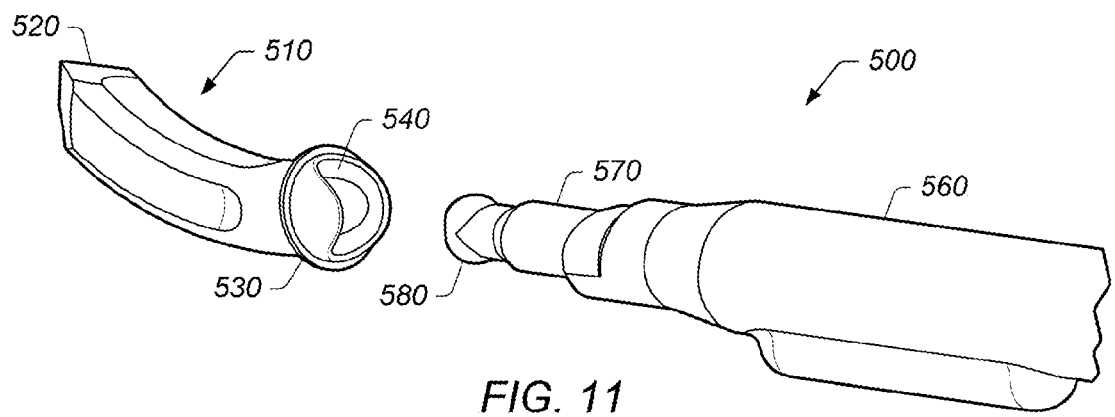
FIG. 11 depicts a diagram of a perspective view of an embodiment of an anchor for a spinal implant with an anchor insertion instrument with a coupling member.

In some embodiments, an intervertebral implant system may include an intervertebral implant 100 and an anchor insertion instrument 500. In some embodiments, the intervertebral implant may include a body comprising a superior surface and an inferior surface. At least a portion of the superior surface may be function to contact an endplate of an upper adjacent vertebra during use. The inferior surface may function to contact an endplate of a lower adjacent vertebra during use. The intervertebral implant may include a first anchor channel. A first end of the first anchor channel may be coupled to the anterior end and a second end of the first anchor channel extends through the inferior or superior face of the body. The intervertebral implant may include a first anchor 510 positionable in the first anchor channel. The first anchor may include a first end 520 and a second end 530. The first end may include a tapered end. The second end may include an elongated slot 540 coupled to an expanded opening 550 including a first dimension (e.g., depicted in FIG. 11). The elongated slot comprises a first height and a first width. The first height may be greater than the first width.

Figure 12:
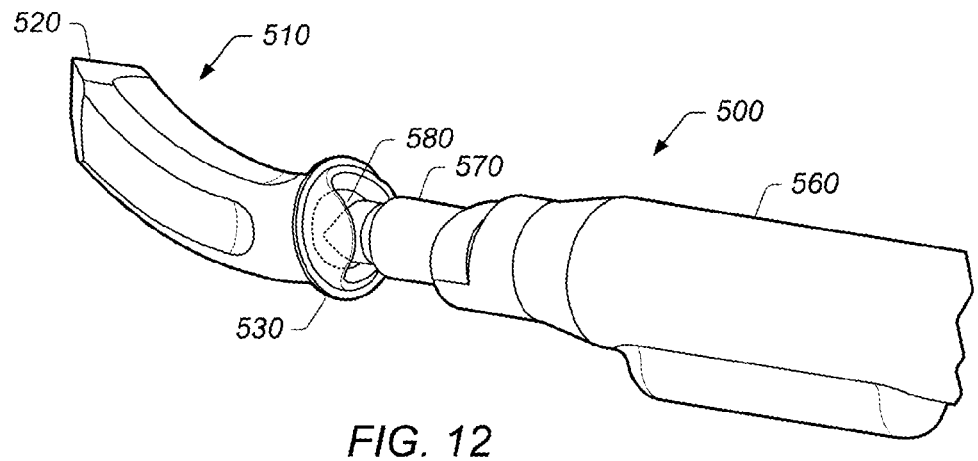
FIG. 12 depicts a diagram of a perspective view of an embodiment of an anchor for a spinal implant with an anchor insertion instrument with a coupling member inserted in an elongated slot in a head of the anchor in an unengaged position.
Figure 13:
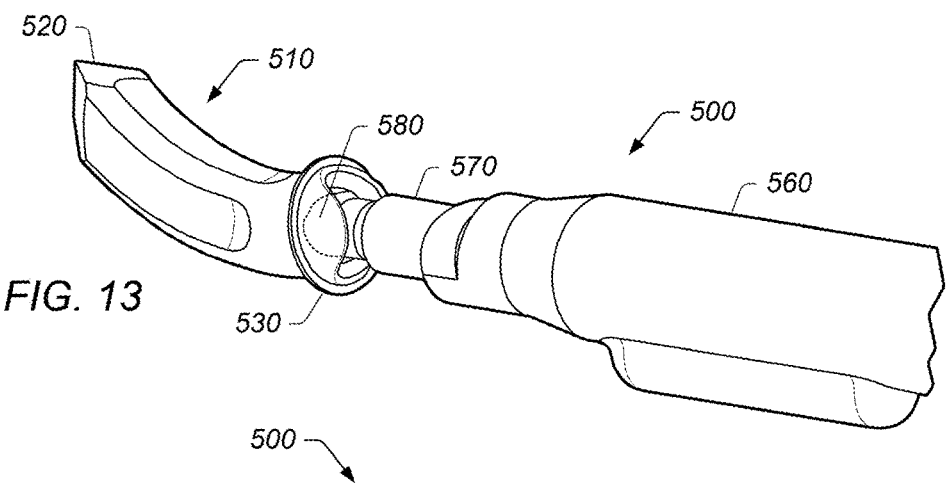
FIG. 13 depicts a diagram of a perspective view of an embodiment of an anchor for a spinal implant with an anchor insertion instrument with a coupling member inserted in an elongated slot in a head of the anchor in an engaged position.
Figure 14:
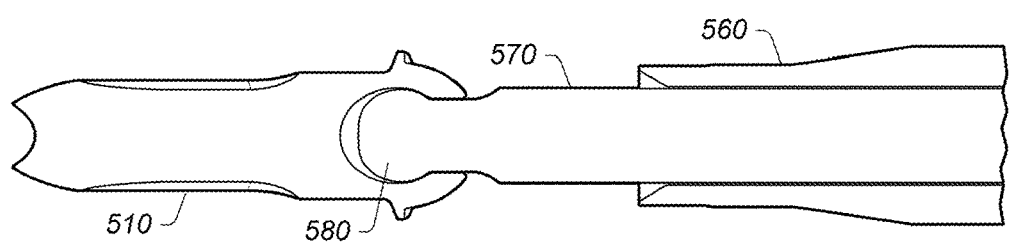
FIG. 14 depicts a diagram of a cross-sectional view of an embodiment of an anchor for a spinal implant with an anchor insertion instrument with a coupling member inserted in an elongated slot in a head of the anchor in an engaged position.
Figure 15:
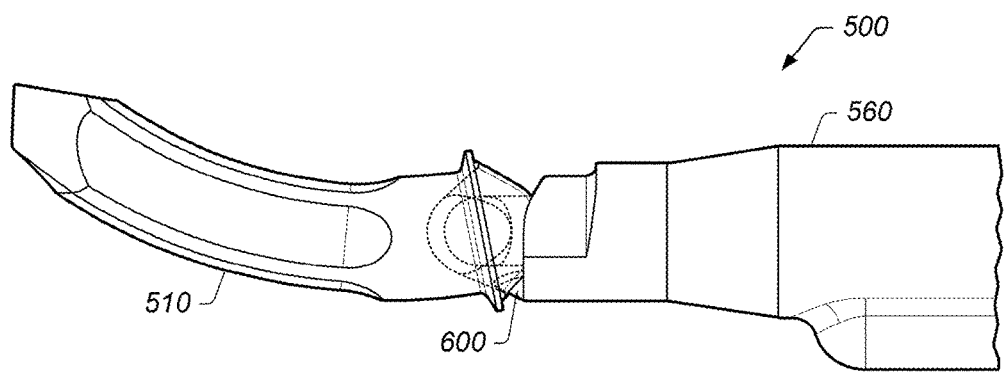
FIG. 15 depicts a diagram of a side view of an embodiment of an anchor for a spinal implant with an anchor insertion instrument with a coupling member inserted in an elongated slot in a head of the anchor in an engaged position with a second end of the anchor abutting a distal end of an elongated conduit.

In some embodiments, the anchor insertion instrument 500 may include an elongated conduit 560. The anchor insertion instrument may include an elongated shaft 570 positioned in the elongated conduit 560 (e.g., depicted in FIG. 11). The elongated shaft may be movable within the elongated conduit from a first position (e.g., as depicted in FIG. 14) to a second position (e.g., as depicted in FIG. 15). The anchor insertion instrument may include a coupling member 580 coupled to a distal end 590 of the elongated shaft. The coupling member may include a second height and a second width. The second height may be greater than the second width. The second height may be less than the first height and the second height may be greater than the first width. The first dimension may be greater than the second height. The coupling member 580 may be dimensioned to fit through the elongated slot 540 when the longitudinal axis of the coupling member is in alignment with the elongated slot (e.g., as depicted in FIG. 12). Upon the coupling member 580 being positioned into the expanded opening 550 the coupling member and expanded opening are dimensioned relative to one another to allow the coupling member to be rotated within the expanded opening. The coupling member may be rotated using the elongated shaft coupled to the coupling member. Upon the coupling member be rotated such that the longitudinal axis of the coupling member is misaligned with the elongated slot (e.g., as depicted in FIG. 13) the coupling member is inhibited from being extracted back through the elongated slot.

Figure 16:
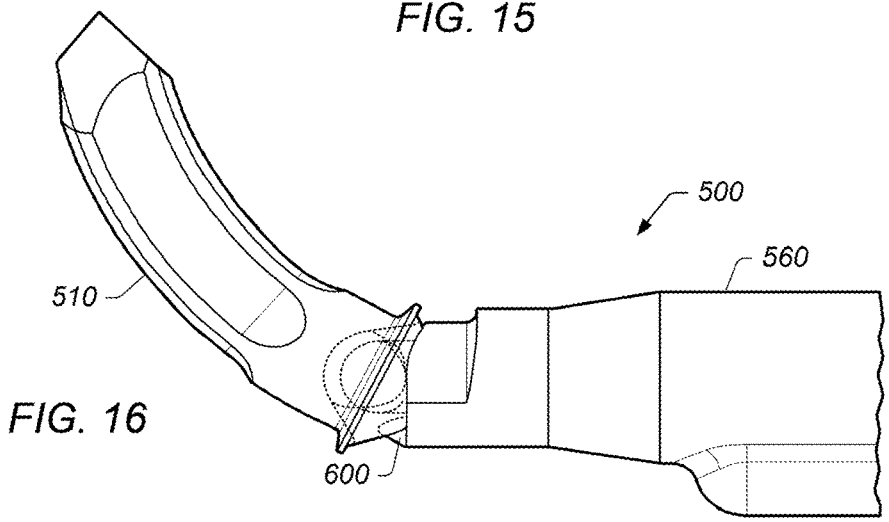
FIG. 16 depicts a diagram of a side view of an embodiment of an anchor for a spinal implant with an anchor insertion instrument with a coupling member inserted in an elongated slot in a head of the anchor in an engaged position with a second end of the anchor abutting a distal end of an elongated conduit. The anchor has rotated relative to the insertion instrument with assistance from complementary surfaces on the anchor head and the distal end of the elongated conduit.

Upon coupling the coupling member to the anchor, the elongated shaft may be retracted within the elongated conduit from the first position to the second position (e.g., as depicted in FIGS. 14-15). In some embodiments, the elongated shaft may be biased towards the second position (e.g., spring loaded). Retracting the elongated shaft to the second position abuts the second end of the anchor to a distal end of the elongated conduit. The second end of the anchor and the distal end of the elongated conduit may include complementary shaped surfaces. In some embodiments, the second end of the anchor includes a convex surface and the distal end of the elongated conduit includes a concave surface complementary to the convex surface. The spherical head of the curved anchor rotates about the concave tip of the distal end of the elongated conduit (e.g., as depicted in FIG. 16). The spherical head of the anchor and the concave surface of the distal end of the elongated conduit allows for articulation of the anchor about the inserter instrument. When anchor engages the screw hole, which is angled toward the vertebral body, the anchor rotates about the distal end of the elongated conduit's concave tip and allows the anchor to be impacted perpendicular to the anterior end.

In some embodiments, the anchor insertion instrument 500 may include an aligner 600. The aligner may function to inhibit rotational movement of the anchor relative to the conduit 560 when the second end of the anchor abuts the distal end of the elongated conduit. The aligner 600 may be positionable in the elongated slot 540 when the second end of the anchor abuts the distal end of the elongated conduit. When the aligner 600 is positioned in the elongated slot the anchor is inhibited from rotating relative to the conduit 560 inhibiting disengagement of the coupling member 580 from the anchor 510 except when desired by the user.

In some embodiments, a method may include implanting an intervertebral implant within an intervertebral space between endplates of adjacent vertebra. The method may include implanting an intervertebral implant between an upper adjacent vertebra and a lower adjacent vertebra such that a superior surface of a body of the intervertebral implant contacts an endplate of the upper adjacent vertebra and an inferior surface of the body contacts an endplate of the lower adjacent vertebra. The method may include inserting a coupling member of an anchor insertion instrument through an elongated slot and into an expanded opening coupled to the elongated slot in a second end of a first anchor, wherein the first anchor comprises a first end. The method may include rotating the coupling member within the expanded opening such that the coupling member is inhibited from extraction through the elongated slot of the first anchor. The method may include retracting an elongated shaft coupled, positionable in an elongated conduit, to the coupling member such that the second end of the first anchor abuts a distal end of the elongated conduit. The method may include conveying the first anchor through a first anchor channel in a body of the implant using the anchor insertion instrument. A first end of the first anchor channel may be coupled to the anterior end and a second end of the first anchor channel extends through the inferior or the superior face of the body. The method may include coupling the body to the upper or the lower adjacent vertebra using the first anchor.

In some embodiments, the method may include allowing articulation of the first anchor relative to the insertion instrument when the second end of the first anchor abuts a distal end of the elongated conduit. The second end of the first anchor may be substantially spherical. The distal end of the elongated conduit may be substantially concave.

Figure 17A:
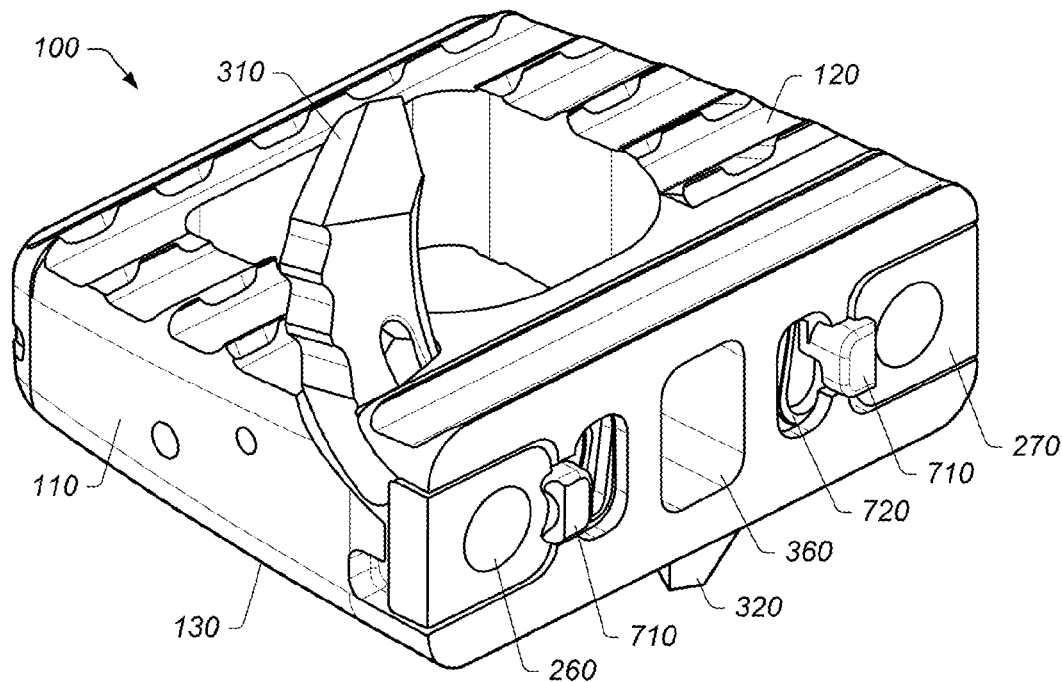
FIGS. 17A-B depict diagrams of a top rear perspective view of embodiments of a spinal implant with anchors in an engaged position.
Figure 17B:
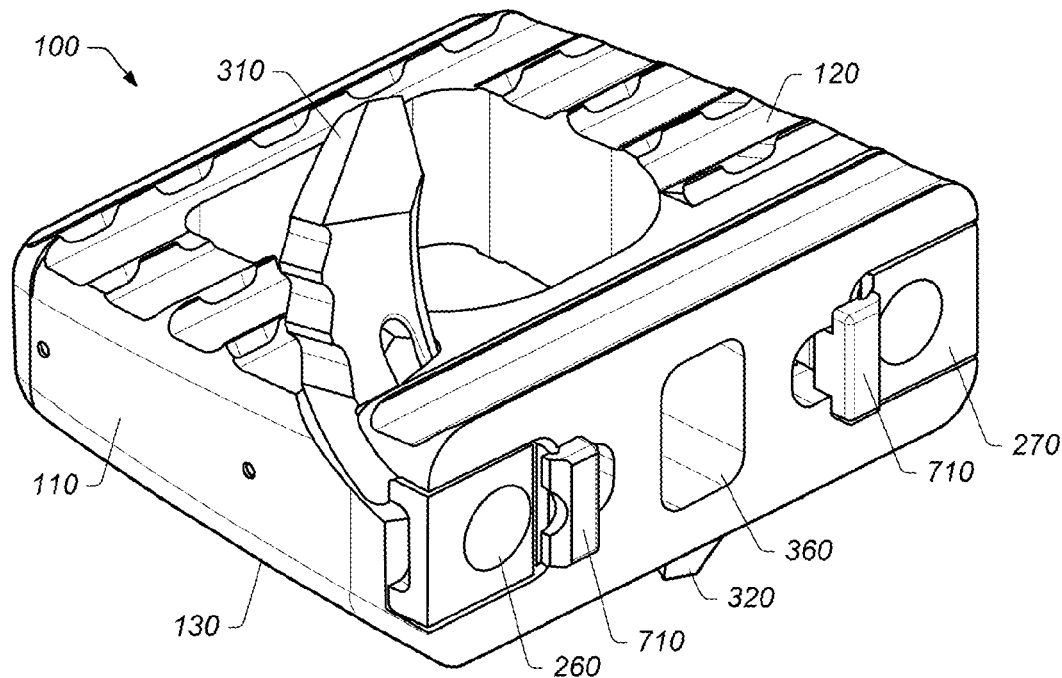
Figure 18A:
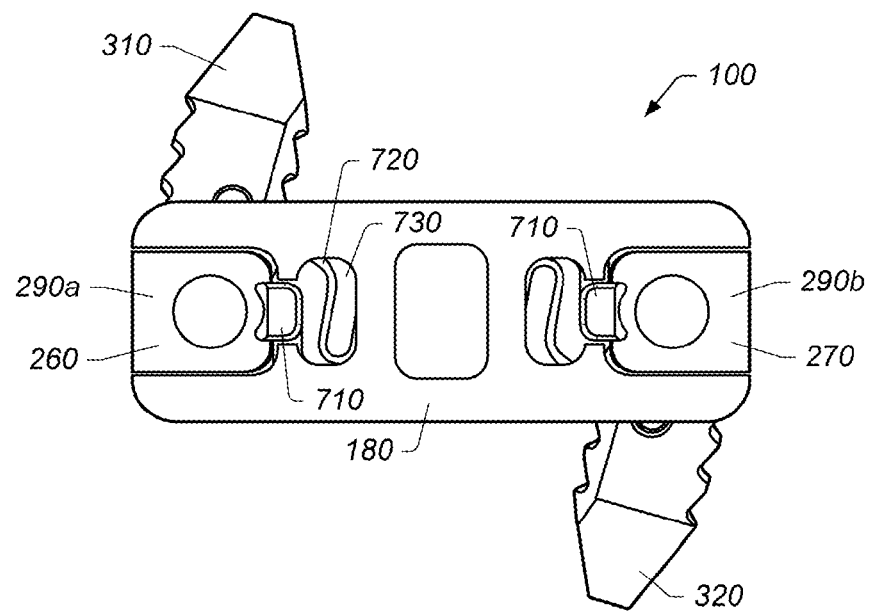
FIGS. 18A-D depict diagrams of a rear view of embodiments of a spinal implant with anchors in an engaged position.
Figure 18B:
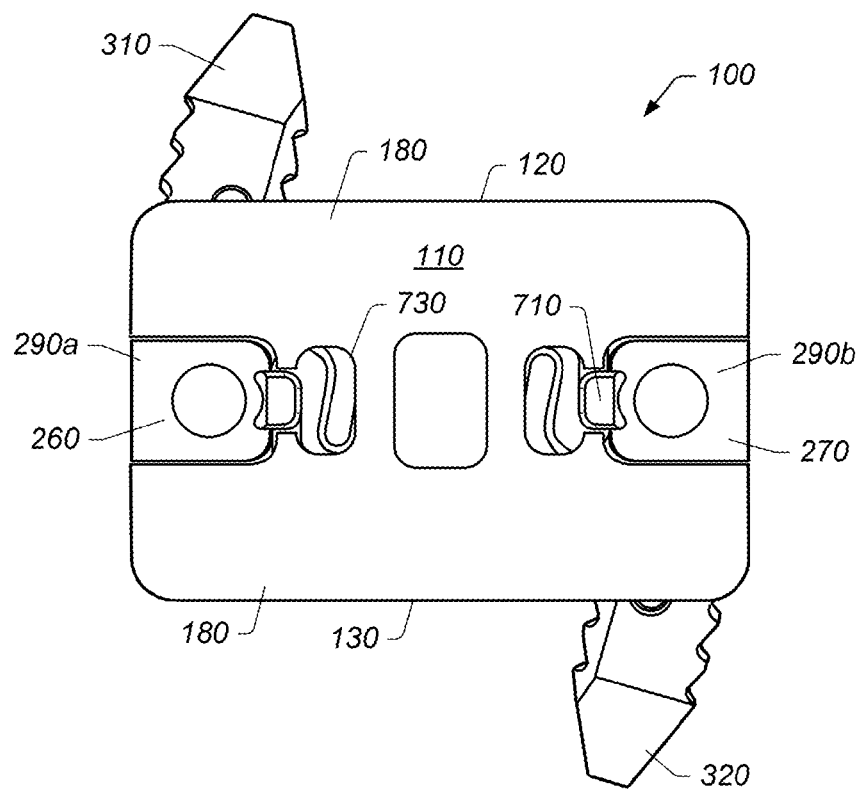
Figure 18C:
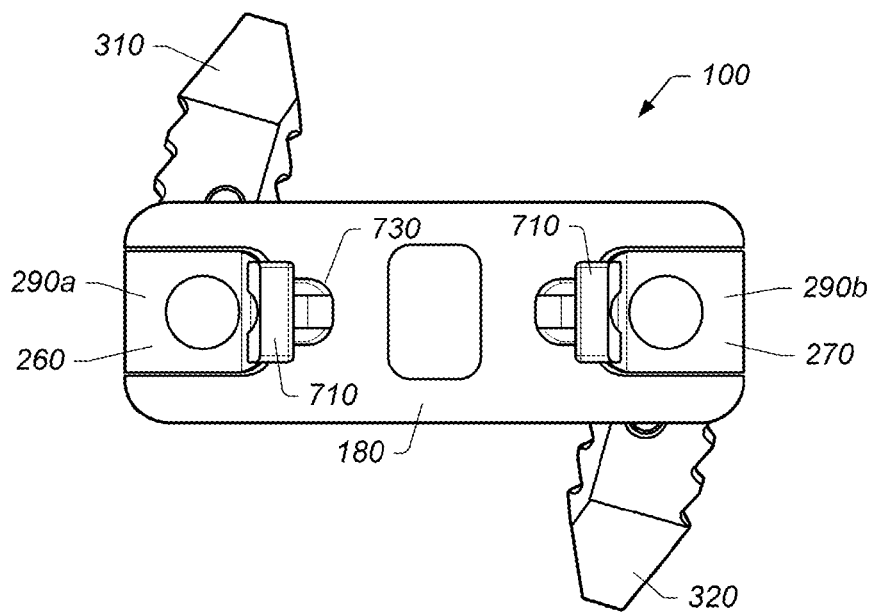
Figure 18D:
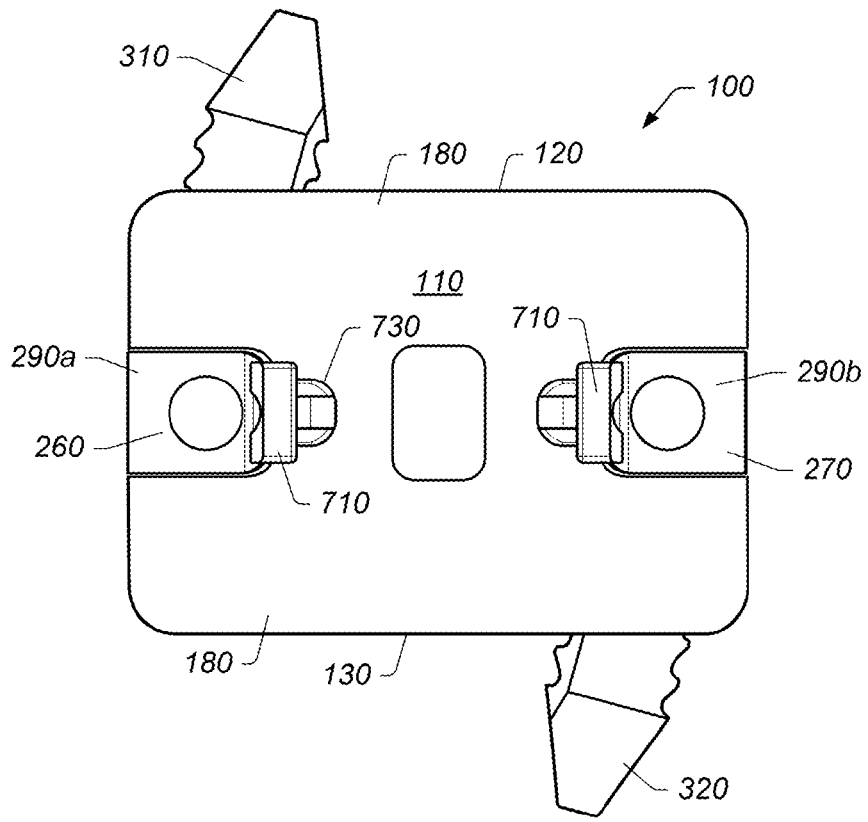
Figure 19A:
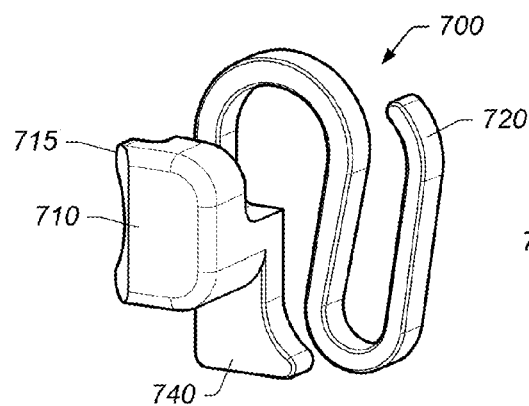
FIGS. 19A-B depict diagrams of a perspective view of embodiments of a locking member of a locking mechanism for a spinal implant.
Figure 19B:
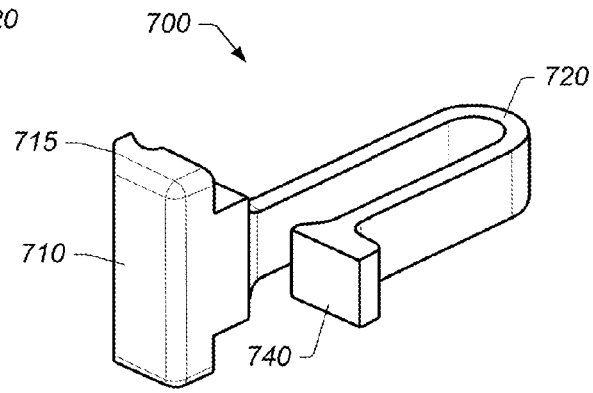

Locking Intervertebral Implant Embodiments:

At least portions of embodiments described herein below may combined in any numbers of ways with one or more portions of embodiments of the implant described herein below. In some embodiments, the implant (e.g., depicted in FIGS. 17-18D) may include a first locking mechanism 700 (e.g., depicted in FIGS. 19A-B) which inhibits, during use, the first guide member 260 from moving from the second position (e.g., depicted in FIGS. 24A-B) to the first position (e.g., depicted in FIGS. 23A-B) upon activation of the first locking mechanism. In some embodiments, the first locking mechanism 700 may include a locking member 710 and a resilient member 720 (e.g., depicted in FIGS. 19A-B). The resilient member may bias the locking member in a locked position. In some embodiments, the locking member 710 may function as a visual locking indicator for a user who is implanting the implant 100. A position of the locking member 710 may allow a user to visually determine whether or not the locking member has been activated and as such if the implant has been properly deployed.

The resilient member 720 may be able to recoil or spring back into shape after bending, stretching, or being stretched. The resilient member may be formed from a biocompatible material which returns to its original shape upon being distorted, for example, as a result of external forces. The resilient member 720 may return to its original form upon distortion due to the innate properties of the materials used to form the resilient member. The resilient member may be in the form of a spring or spring like member.

The resilient member 720 may be coupled to the locking member 710 of the locking mechanism 700. The resilient member 720 may be coupled to the body 110 of the implant 100. In some embodiments, the resilient member 720 may be positioned in an opening 730 in a proximal end of the body of the implant. The opening may be sized to compress the resilient member within the opening and hold the resilient member in via, for example, a friction fit. In some embodiments, a coupling member 740 (e.g., depicted in FIGS. 19A-B) may form a portion of the locking mechanism 700 which may, for example, inhibit the resilient member from exiting the opening 730 (e.g., depicted in FIG. 18A-D). The locking member 710 may be coupled to the resilient member such that at least a portion of the locking member extends outside of the opening 730. The locking member may slide along a proximal surface 180 (e.g., in some embodiments an anterior end during use) of the body 110 of the implant 100 (e.g., depicted in FIG. 18A-D). The resilient member 720 may bias the locking member 710 in a locked position such that at least a portion of the locking member covers an opening in the proximal surface 180 of the body 110 of the implant 100. The opening may form a posterior portion of the channel 160. When in the locked position the locking member inhibits, during use, the guide member 260 from moving from the second position (e.g., depicted in FIGS. 24A-B), the first end 290a of the guide member substantially flush with the proximal or anterior end 180 of the body 110, to the first position (e.g., depicted in FIGS. 23A-B), a first end of the guide member extending from the proximal or anterior end of the body, inhibiting the anchor 310 from becoming unengaged from an adjacent vertebrae when the anchor is deployed (e.g., depicted in FIGS. 24A-B).

Figure 20A:
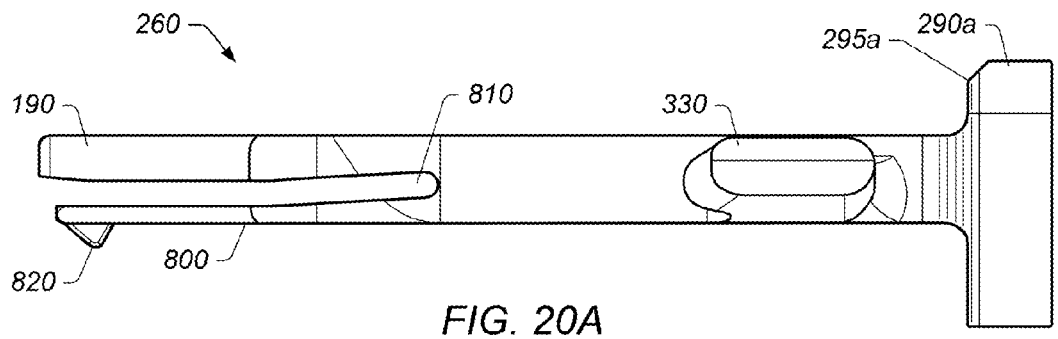
FIGS. 20A-B depict diagrams of a side view of embodiments of a guide member for a spinal implant.
Figure 23A:
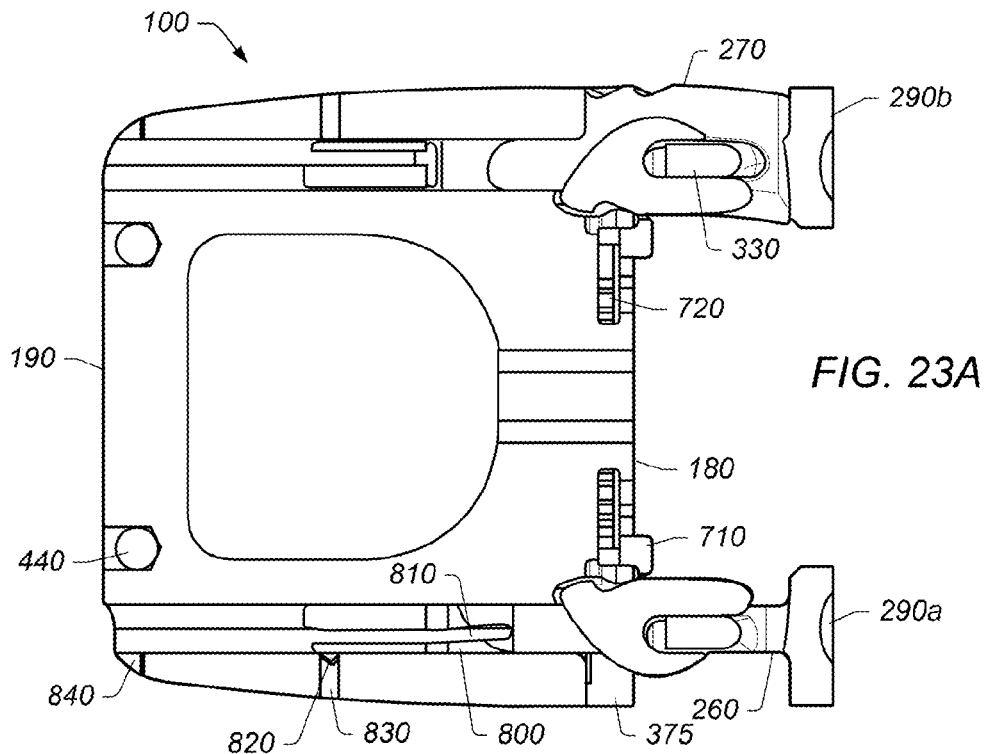
FIGS. 23A-B depict diagrams of a top cross sectional view of embodiments of a spinal implant with anchors in an unengaged position.
Figure 23B:
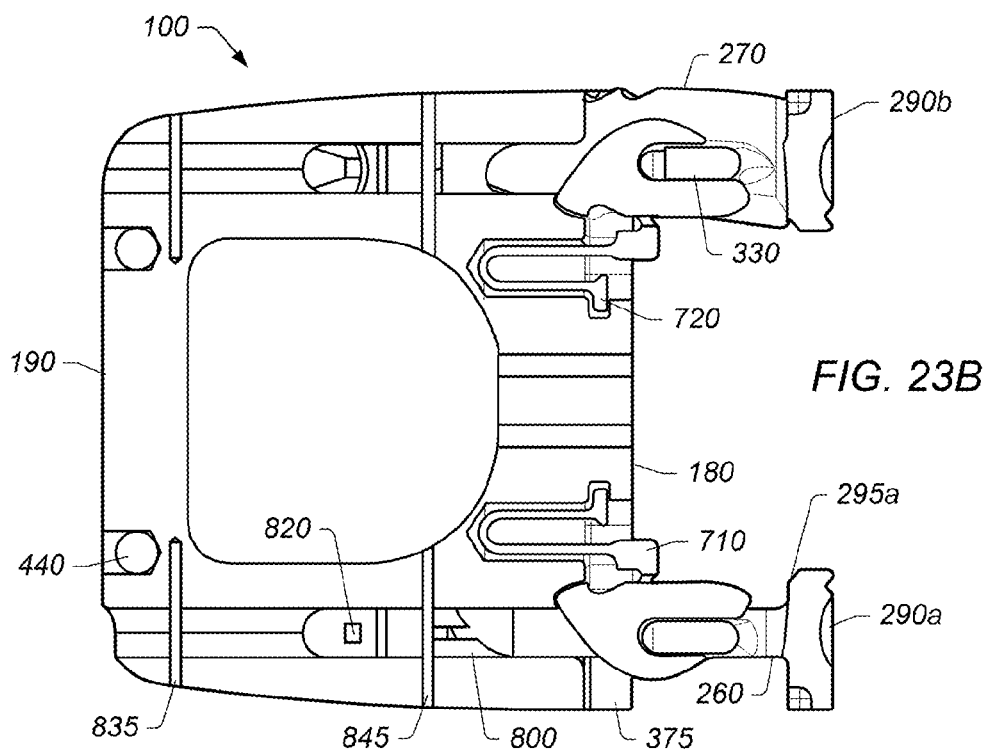
Figure 24A:
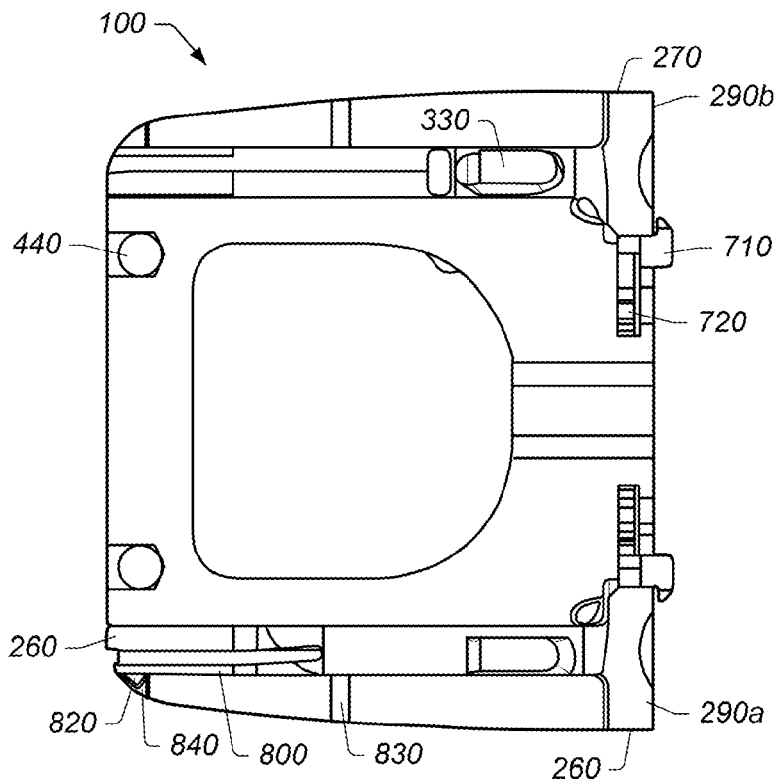
FIGS. 24A-B depicts a diagram of a top cross sectional view of an embodiment of a spinal implant with anchors in an engaged position.
Figure 24B:
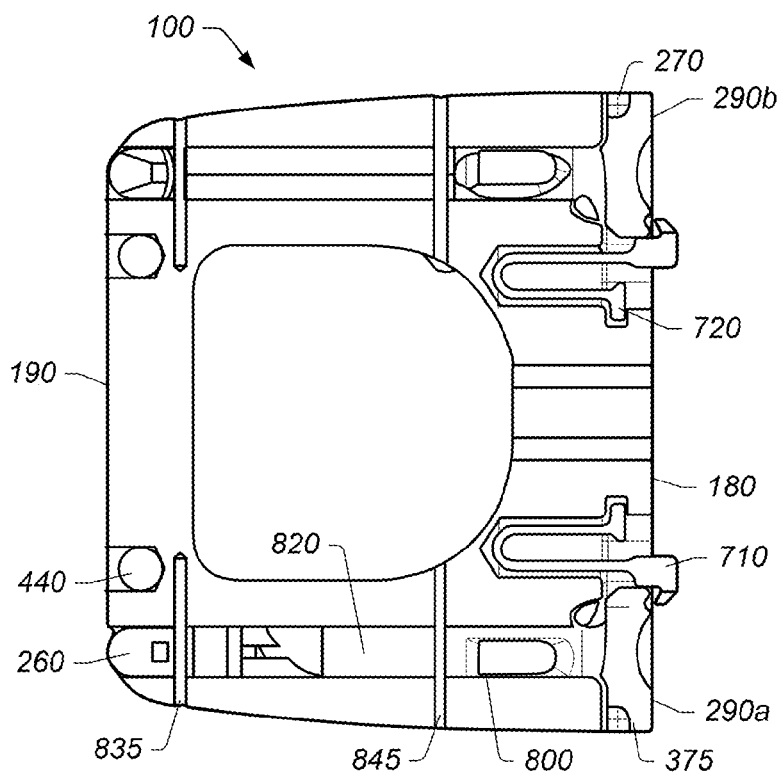

In some embodiments, the locking member may include an angled edge 715 (e.g., depicted in FIGS. 19A-B) on an exterior (relative to the implant) face and on a side of the locking member facing the opening in the proximal surface of the body of the implant forming a portion of the channel. The first end of the guide member may include an angled edge 295a (e.g., as depicted in FIGS. 20A and 23B) on an interior (relative to the implant) face and on a side of the first end of the guide member facing the angled edge of the locking member. The two angled surfaces may be complementary such that when the guide member is moved from the first position (e.g., as depicted in FIGS. 23A-B) to the second position (e.g., as depicted in FIGS. 24A-B) the angled surface of the first end of the guide member translates the longitudinal force of the guide member to a lateral force for the locking member. The lateral force moves the locking member form a locked position to an unlocked position allowing the first end of the guide member to pass by the locking member. Upon the first end of the guide member passing by the locking member, the resilient member may provide a lateral force counter to the first lateral force moving the locking member from the unlocked position to the locked position (e.g., such that at least a portion of the locking member covers a portion of the channel and the first end of the guide member.

In some embodiments, the first ends 290a-b of the guide members may be shaped such that the first end is inhibited from moving substantially beyond the proximal (e.g., anterior) end 180 of the body 110 inhibiting movement of the first guide member towards the distal (e.g., posterior) end 190. The first end of the guide members may fit within a recess 375 of the anterior end and as such be shaped to fit substantially flush with the anterior end (e.g., depicted in FIGS. 23A-24B).

Figure 20B:
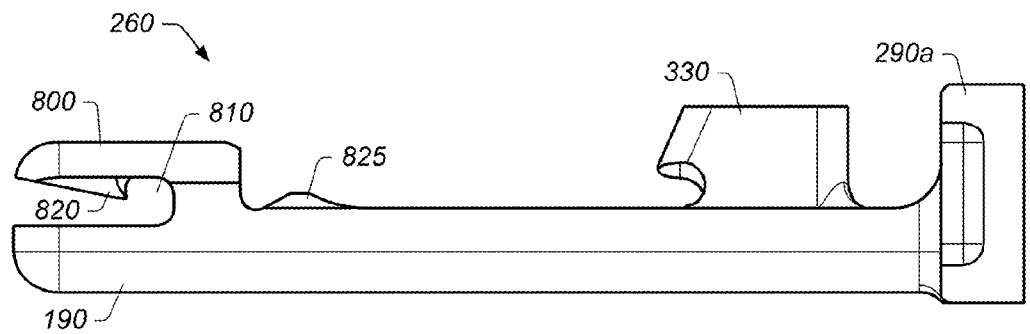

In some embodiments, the first guide member 260 may include an at least partially flexible second member 800 (e.g., as depicted in FIGS. 20A-B). The second member 800 may be positioned towards a distal end 190 (e.g., posterior end) of the first guide member 260. In some embodiments, the second member may flex toward the first guide member when force is applied to the second member (e.g., as depicted in FIG. 20A, there may be an opening 810 between the distal end 190 of the first guide member 260 and the second member 800 allowing the second member 800 room to move). In some embodiments, the second member may be more rigid (e.g., as depicted in FIG. 20B).

In some embodiments, the second member 800 may include an engager 820 (e.g., as depicted in FIGS. 20A-B). In some embodiments, the engager may be positioned on a side of the second member opposite to the first guide member (e.g., as depicted in FIG. 20A). The engager may interact, during use, with a first surface feature 830 to inhibit movement of the first guide member 260 in the first channel 160. The engager may interact, during use, with a first surface feature to inhibit movement of the first guide member in the first channel from the first position to the second position. The engager may interact, during use, with a first and/or a second surface feature to inhibit movement of the first guide member in the first channel. The engager 820 may interact, during use, with a second surface feature 840 to inhibit movement of the first guide member in the first channel from the second position to the first position.

In some embodiments, the engager 820 may include an elevated feature extending from the second member 800. In some embodiments, the first 830 and/or second 840 feature along an interior surface of the channel 160 may include an opening or depression. The opening or depression may have a complementary shape to the engager. As such, in some embodiments, the second member may flex towards the guide member while moving through the channel (e.g., as the engager may be too large to move through the channel without the second member flexing inward). The surface feature may engage the engager and inhibit further movement through the channel at least without additional force being applied by the user. The surface feature may allow the second member to flex outward, away from the guide member as the engager engages (e.g., enters) the surface feature.

In some embodiments, the opening and/or the engager may be shaped such that the engager's exit from the opening is facilitated when the guide member is moving in a first direction relative the engager's exit from the opening when the guide member is moving in an opposing second direction. For example, when the guide member is moved from a first position to a second position the engager may move out of the first surface feature and into the second surface feature easier relative to (hence requiring more force exerted by a user) moving the guide member from the second position to the first position (hence biasing the implant in an engaged state with adjacent vertebrae during use).

In some embodiments, the engager may be positioned on a side of the second member facing the first guide member (e.g., as depicted in FIG. 20B). The engager may interact, during use, with a first feature 835 (the first feature may include an elongated member stretching across at least a portion of the first channel) to inhibit movement of the first guide member 260 in the first channel 160. The engager may interact, during use, with a first feature to inhibit movement of the first guide member in the first channel from the second position to the first position. The engager may be sloped to allow the engager to more easily slide over the first feature when the first guide member moves from the first position to the second position. However, upon the first guide member reaching the second position or at least substantially adjacent the second position the engager may engage the first feature to inhibit movement of the first guide member in the first channel from the second position to the first position.

The engager may interact, during use, with a first feature to inhibit movement of the first guide member in the first channel.

In some embodiments, an engager 825 may interact, during use, with a second feature 845 (the first feature may include an elongated member stretching across at least a portion of the first channel) to inhibit movement of the first guide member in the first channel from the first position to the second position. In some embodiments, the engager 825 may interact with the second feature 845 only to slightly inhibit movement of the first guide member in the first channel from the first position to the second position such that the first guide member is not accidentally deployed prematurely during surgery.

In some embodiments, at least a portion of the second member 800 may interact with the second feature 845 to inhibit extraction of the first guide member from the first channel (e.g., as depicted in FIG. 23B, out of the proximal (e.g., anterior) end 180 of the body 110).

Figure 21:
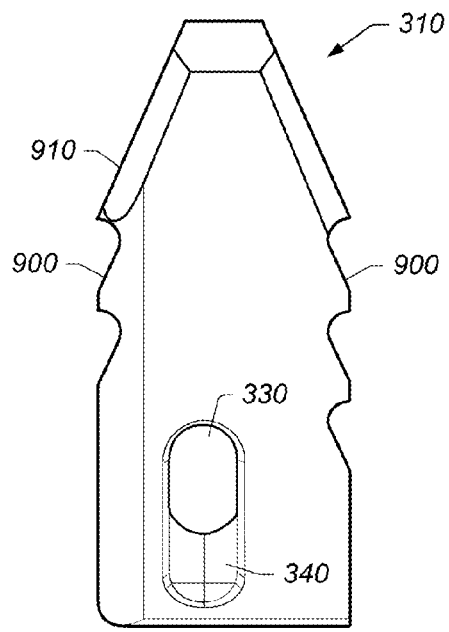
FIG. 21 depicts a diagram of a top view of an embodiment of an anchor for a spinal implant.

In some embodiments, the first guide member 260 may include a coupling member 330 adjacent the first end 290a of the guide member (e.g., depicted in FIGS. 20-21). The first anchor 310 may include an opening 340 into which the coupling member is positionable (e.g., depicted in FIG. 21). The coupling member may include a post. The opening may be sized relative to the post to allow movement of the anchor relative to the guide member.

In some embodiments, coupling member 330 may interact with second feature 845 to inhibit movement of the first guide member 260 from moving towards the posterior end 190 past the second position.

In some embodiments, an anchor may include a plurality of ridges 900 along at least one edge 910 of the anchor 310 (e.g., depicted in FIG. 21). In some embodiments, an anchor may include a plurality of ridges along at least two opposing edges of the anchor. At least some of the plurality of ridges may be oriented in a direction substantially opposing to a direction of insertion of the first anchor in the adjacent vertebra during use (e.g., depicted in FIG. 21). The orientation of the ridges may facilitate insertion of the first anchor in adjacent vertebra while inhibiting extraction of the first anchor from adjacent vertebra.

Figure 22A:
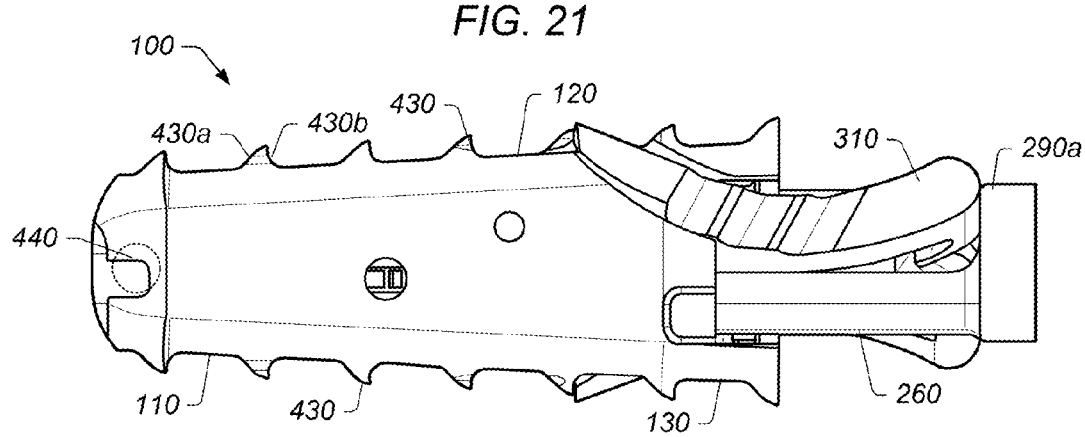
FIGS. 22A-B depict diagrams of a side view of embodiments of a spinal implant with anchors in an unengaged position.
Figure 22B:
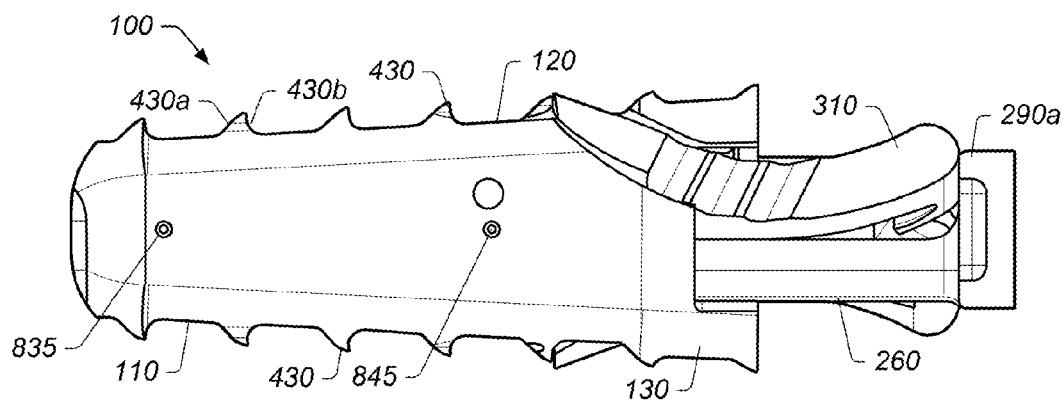

Superior and/or inferior surfaces of the implant may include various features to facilitate engagement of the surfaces with endplates of adjacent vertebrae. In some embodiments, the implant may include a plurality of surface deformations positioned on the inferior surface and/or the superior surface. Surface deformations may include protrusions. For example (e.g., depicted in FIGS. 22A-B) superior surface 120 and/or inferior surface 130 of body 110 may include protrusions (e.g., teeth) 430 extending there from. During use, teeth 430 may extend/penetrate into adjacent boney structure of the upper and lower adjacent vertebrae. Such penetration may help to fix a position of body 110, and, thus implant 100, relative to the vertebrae. Fixing or otherwise stabilizing the implant may reduce the likelihood of implant 100 being expelled from within the intervertebral space, and may promote bone attachment to and/or through implant 100.

In some embodiments, protrusions 430 may include unidirectional teeth that facilitate forward insertion of the members, but inhibit back-out of the members. For example, in the illustrated embodiment, teeth 430 include a ramped leading surface 430a and a substantially vertical trailing edge 430b (e.g., depicted in FIGS. 22A-B). Thus, forward advancement of the members may be facilitated as boney structure of the vertebrae slides over ramped leading surface 430a of teeth 430 and backward advancement may be inhibited by substantially vertical trailing edge 430b hooking into or otherwise engaging the boney structure of the vertebrae.

In some embodiments, the body may include an opening 350 extending from the superior surface to the inferior surface (e.g., depicted in FIGS. 23-24). The opening may hold biological material during use. In some embodiments, opening 350 may be filled with a substance/material to facilitate bone growth/fusion. Once implant 100 is implanted, the opening may facilitate a column of bone growth between the adjacent vertebrae through the opening 350. In some embodiments, an opening (e.g., opening 350) may function as a graft window containing bone chips and/or materials which facilitate tissue (e.g., bone) growth. The opening 350 depicted in FIGS. 23-24 may include an increased radius relative to the opening 350 depicted in FIGS. 2A-B. The increased radius may provide for increased strength of the implant.

In some embodiments, one or more portions of the implant 100 may include markers 440 (e.g., depicted in FIGS. 22-24). Markers may be used to assess a position of one or more portions of the implant during implantation in a subject. A portion of the implant may include none, one or multiple markers. Markers may provide radiographic opacity. Markers may be biocompatible. Markers may be of any size or shape. In some embodiments, a system may have multiple markers with different shapes in order to more easily identify different portions of the system and/or an orientation of one or more portions of the implant. In some embodiments, one or more markers may be formed from gold or tantalum.

In some embodiments, the implant 100 may be made available in multiple sizes to accommodate different patients. For example, FIGS. 18B and D depicts an embodiment of implant 100 which is thicker in dimension than the embodiment depicted in FIGS. 18A and B.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An intervertebral implant, comprising:
   a body comprising a superior surface and an inferior surface, wherein at least a portion of the superior surface is configured to contact an endplate of an upper adjacent vertebra during use, and wherein the inferior surface is configured to contact an endplate of a lower adjacent vertebra during use;
   a first channel extending from an anterior end towards a posterior end of the body;
   a first anchor channel, wherein a first end of the first anchor channel is coupled to the first channel adjacent the anterior end and a second end of the first anchor channel extends through a superior or inferior face of the body;
   a first guide member positionable in the first channel, wherein the first guide member is movable from a first position, a first end of the first guide member extending from the anterior end of the body, to a second position, the first end of the first guide member substantially flush with the anterior end of the body, during use;
   a first anchor coupled to the first end of the first guide member, wherein when the first guide member moves from the first position to the second position the first anchor is conveyed through the first anchor channel and is capable of coupling the body to the upper or lower adjacent vertebra during use; and
   a first locking mechanism which inhibits, during use, the first guide member from moving from the second position to the first position upon activation of the first locking mechanism.

2. The implant of claim 1, wherein the first locking mechanism visually indicates, during use, to a user if the first locking mechanism has been activated.

3. The implant of claim 1, further comprising:
   a second channel extending from the anterior end to the posterior end of the body, wherein the first and the second channels are positioned on substantially opposing sides of the body;
   a second anchor channel, wherein a first end of the second anchor channel is coupled to the second channel adjacent the anterior end and a second end of the second anchor channel extends through the superior or the inferior face of the body;
   a second guide member positionable in the second channel, wherein the second guide member is movable from a first position, a first end of the guide member extending from the anterior end of the body, to a second position, the first end of the guide member substantially flush with the anterior end of the body, during use;
   a second anchor coupled to the first end of the second guide member,
   wherein when the second guide member moves from the first position to the second position the second anchor is conveyed through the second anchor channel and is capable of coupling the body to the upper or the lower adjacent vertebra during use; and
   a second locking mechanism which inhibits, during use, the second guide member from moving from the second position to the first position upon activation of the second locking mechanism.

4. The implant of claim 1, wherein the first locking mechanism comprises:
   a locking member; and
   a resilient member which biases the locking member in a locked position.

5. The implant of claim 1, wherein the first anchor comprises a plurality of ridges along at least one edge of the first anchor, wherein at least some of the plurality of ridges are oriented in a direction substantially opposing to a direction of insertion of the first anchor in the upper or the lower adjacent vertebra during use.

6. The implant of claim 1, wherein the first guide member comprises a second member coupled towards a distal end of the first guide member.

7. The implant of claim 1, wherein the first guide member comprises a second member coupled towards a distal end of the first guide member, wherein the second member comprises an engager, and wherein the engager interacts, during use, with a first feature to inhibit movement of the first guide member in the first channel.

8. The implant of claim 1, wherein the first guide member comprises:
   a second member positioned towards a distal end of the first guide member, wherein the second member comprises an engager, and wherein the engager interacts, during use, with a first feature to inhibit movement of the first guide member in the first channel; and
   a stop positioned towards a distal end of the first guide member and proximal to the second member, wherein the stop interacts, during use, with a second feature to inhibit movement of the first guide member in the first channel.

9. The implant of claim 1, wherein the first guide member comprises:
   a second member positioned towards a distal end of the first guide member, wherein the second member comprises an engager, and wherein the engager interacts, during use, with a first feature to inhibit movement of the first guide member in the first channel from the second position to the first position; and
   a stop positioned towards a distal end of the first guide member and proximal to the second member, wherein the stop interacts, during use, with a second feature to inhibit movement of the first guide member in the first channel from the first position to the second position.

10. The implant of claim 9, wherein the first and/or second feature comprises an elongated member positioned at least partially in the first channel.

11. The implant of claim 1, wherein substantially all of an outer perimeter of the body of the implant is positionable within the outer perimeter of the upper and lower adjacent vertebrae after installation.

12. The implant of claim 1, wherein the first guide member comprises a coupling member adjacent the first end of the guide member, and wherein the first anchor comprises an opening into which the coupling member is positionable.

13. The implant of claim 1, wherein the first guide member comprises a coupling member adjacent the first end of the guide member, and wherein the coupling member comprises a post.

14. The implant of claim 1, wherein the anterior end comprises an opening, and wherein the opening is configurable to couple to an insertion instrument.

15. A method of implanting an intervertebral implant within an intervertebral space between endplates of adjacent vertebra, comprising the steps:
   implanting an intervertebral implant between an upper adjacent vertebra and a lower adjacent vertebra, the intervertebral implant comprising:
      a body comprising a superior surface and an inferior surface, wherein at least a portion of the superior surface is configured to contact an endplate of an upper adjacent vertebra during use, and wherein an inferior surface is configured to contact an endplate of a lower adjacent vertebra during use;
      a first channel extending from an anterior end towards a posterior end of the body;
      a first anchor channel, wherein a first end of the first anchor channel is coupled to the first channel adjacent the anterior end and a second end of the first anchor channel extends through a superior or inferior face of the body;
      a first guide member positionable in the first channel, wherein the first guide member is movable from a first position, a first end of the first guide member extending from the anterior end of the body, to a second position, the first end of the first guide member substantially flush with the anterior end of the body, during use;
      a first anchor coupled to the first end of the first guide member, wherein when the first guide member moves from the first position to the second position the first anchor is conveyed through the first anchor channel and is capable of coupling the body to the upper or lower adjacent vertebra during use; and
      a locking mechanism which inhibits, during use, the first guide member from moving from the second position to the first position upon activation of the locking mechanism, wherein the intervertebral implant is implanted such that the superior surface of the body of the intervertebral implant contacts the endplate of the upper adjacent vertebra and the inferior surface of the body contacts the endplate of the lower adjacent vertebra;
   conveying the first guide member through the first channel from the first position, the first end of the first guide member extending from the anterior end of the body, to the second position, the first end of the first guide member substantially flush with the anterior end of the body, during use;
   conveying the first anchor through the first anchor channel when the first guide member moves from the first position to the second position, wherein the first end of the first anchor channel is coupled to the first channel adjacent the anterior end and a second end of the first anchor channel extends through the superior and/or the inferior face of the body;
   coupling the body to at least one of the adjacent vertebrae using the first anchor; and
   inhibiting the first guide member from moving from the second position to the first position upon activation of the locking mechanism.

16. The method of claim 15, further comprising biasing a locking member of the locking mechanism in a locked position using a resilient member of the locking mechanism.

17. The method of claim 15, further comprising:
   engaging a first feature using an engager of a second member coupled towards a distal end of the first guide member; and
   inhibiting movement of the first guide member in the first channel using the engaged engager.

18. The method of claim 15, further comprising:
   engaging a first feature using an engager of a second member coupled towards a distal end of the first guide member;
   inhibiting movement of the first guide member in the first channel from the second position to the first position using the engaged engager; and
   interacting a stop with a second feature such that movement of the first guide member is inhibited in the first channel from the first position to the second position, wherein the stop is positioned towards a distal end of the first guide member and proximal to the second member.

19. The method of claim 18, wherein the first and/or second feature comprises an elongated member positioned at least partially in the first channel.

20. The method of claim 15, further comprising coupling an insertion instrument to an opening in the anterior end of the body.

* * * * *